(12) United States Patent
Tedeschi et al.

(10) Patent No.: US 10,083,883 B2
(45) Date of Patent: Sep. 25, 2018

(54) WAFER PROCESSING EQUIPMENT HAVING CAPACITIVE MICRO SENSORS

(71) Applicant: APPLIED MATERIALS, INC., Santa Clara, CA (US)

(72) Inventors: Leonard Tedeschi, San Jose, CA (US); Kartik Ramaswamy, San Jose, CA (US); Daniel Thomas McCormick, San Francisco, CA (US); Robert Paul Meagley, Emeryville, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 15/187,717

(22) Filed: Jun. 20, 2016

(65) Prior Publication Data

US 2017/0365531 A1     Dec. 21, 2017

(51) Int. Cl.
*H01L 21/66*    (2006.01)
*H01L 21/67*    (2006.01)
(Continued)

(52) U.S. Cl.
CPC .............. *H01L 22/26* (2013.01); *G01D 5/24* (2013.01); *G01D 5/2405* (2013.01);
(Continued)

(58) Field of Classification Search
CPC ... H01L 22/26; H01L 22/34; H01L 21/67253; H01L 21/67259; H01L 21/67288;
(Continued)

(56) References Cited

U.S. PATENT DOCUMENTS 5,563,798 A * 10/1996 Berken ................ G05B 19/402
                                                318/640
6,465,271 B1* 10/2002 Ko ........................ G01D 5/2417
                                                361/283.4
(Continued)

FOREIGN PATENT DOCUMENTS

KR          10-1591935 B1     2/2016

OTHER PUBLICATIONS

U.S. Appl. No. 15/068,464, filed Mar. 11, 2016, titled "Wafer Processing Tool Having A Micro Sensor", by inventor Leonard Tedeschi, 66 pages. (filing documents, specification and drawings).
(Continued)

*Primary Examiner* — Marvin Payen
*Assistant Examiner* — Jeremy Joy
(74) *Attorney, Agent, or Firm* — Schwabe, Williamson & Wyatt, P.C.

(57) ABSTRACT

Embodiments include devices and methods for detecting particles, monitoring etch or deposition rates, or controlling an operation of a wafer fabrication process. In an embodiment, a particle monitoring device for particle detection includes several capacitive micro sensors mounted on a wafer substrate to detect particles under all pressure regimes, e.g., under vacuum conditions. In an embodiment, one or more capacitive micro sensors is mounted on a wafer processing tool to measure material deposition and removal rates in real-time during the wafer fabrication process. Other embodiments are also described and claimed.

18 Claims, 9 Drawing Sheets

(51) Int. Cl.
*G01D 5/24* (2006.01)
*G01N 27/22* (2006.01)

(52) U.S. Cl.
CPC ......... *G01N 27/221* (2013.01); *G01N 27/227* (2013.01); *H01L 21/67253* (2013.01); *H01L 22/12* (2013.01)

(58) Field of Classification Search
CPC .................. H01L 22/12; H01L 22/14; G01D 5/24–5/2417; G01N 27/22–27/221; G01N 27/227–27/228; H01J 37/32935; H01J 37/32963; H01J 37/32972
See application file for complete search history.

(56) References Cited

U.S. PATENT DOCUMENTS

| | | | | |
|---|---|---|---|---|
| 6,478,578 | B2* | 11/2002 | Choi | H01L 21/67259 432/253 |
| 6,553,277 | B1* | 4/2003 | Yagisawa | H01J 37/32935 700/108 |
| 6,992,270 | B2* | 1/2006 | Lee | H01L 21/67248 118/724 |
| 7,334,477 | B1* | 2/2008 | Pirkle | H01J 37/32935 219/121.43 |
| 8,104,342 | B2* | 1/2012 | Sun | G03F 7/70616 73/431 |
| 8,224,607 | B2* | 7/2012 | Sakhare | B25J 9/1692 702/95 |
| 2001/0004210 | A1* | 6/2001 | Harada | G01N 27/023 324/224 |
| 2004/0007326 | A1* | 1/2004 | Roche | H01J 37/32935 156/345.24 |
| 2004/0214435 | A1* | 10/2004 | Yuasa | H01J 37/32935 438/689 |
| 2005/0034811 | A1* | 2/2005 | Mahoney | H01J 37/32935 156/345.24 |
| 2005/0213079 | A1* | 9/2005 | Fink | G01N 21/73 356/72 |
| 2005/0268694 | A1* | 12/2005 | Moriya | B08B 9/08 73/28.01 |
| 2005/0284570 | A1* | 12/2005 | Doran | C23F 4/00 156/345.24 |
| 2006/0171848 | A1* | 8/2006 | Roche | G01R 31/2642 422/98 |
| 2006/0234398 | A1* | 10/2006 | Gluschenkov | H01L 21/67294 438/5 |
| 2006/0249729 | A1* | 11/2006 | Mundt | H01L 21/67248 257/48 |
| 2007/0215044 | A1* | 9/2007 | Yamazawa | C23C 16/4401 118/665 |
| 2007/0231460 | A1* | 10/2007 | Ukigaya | C23C 14/042 427/8 |
| 2008/0239314 | A1* | 10/2008 | Bonciolini | H01L 21/67253 356/338 |
| 2008/0241778 | A1 | 10/2008 | Kulp | |
| 2009/0151871 | A1* | 6/2009 | Pease | C23F 4/00 156/345.28 |
| 2009/0322705 | A1* | 12/2009 | Halsey, IV | G06F 3/044 345/174 |
| 2010/0077839 | A1* | 4/2010 | Trentzsch | G01N 27/221 73/31.03 |
| 2010/0129548 | A1* | 5/2010 | Sneh | C23C 16/4409 427/248.1 |
| 2011/0174777 | A1* | 7/2011 | Jensen | H01J 37/32 216/61 |
| 2012/0304928 | A1* | 12/2012 | Koelmel | H01L 21/67115 118/712 |
| 2013/0186177 | A1* | 7/2013 | Palazzotto | B82Y 15/00 73/31.05 |
| 2013/0285736 | A1 | 10/2013 | Loinaz et al. | |
| 2016/0027617 | A1* | 1/2016 | Son | H01J 37/321 156/345.28 |
| 2016/0027675 | A1 | 1/2016 | Ravid et al. | |
| 2016/0049340 | A1* | 2/2016 | Ramachandran | H01L 22/14 257/48 |
| 2017/0016843 | A1* | 1/2017 | Gryska | G01N 27/227 |
| 2017/0199519 | A1* | 7/2017 | Nieters | G05B 23/0235 |

OTHER PUBLICATIONS

U.S. Appl. No. 15/009,705, filed Jan. 28, 2016, titled "Real Time Process Characterization", by inventors Leonard Tedeschi and Kartik Ramaswamy, 76 pages (filing documents, specification and drawings).
Notification of Transmittal of the International Search Report and the Written Opinion Opinion of the International Searching Authority, or the Declaration dated Aug. 31, 2017 for PCT/US2013/037322 (11 Pages).

* cited by examiner

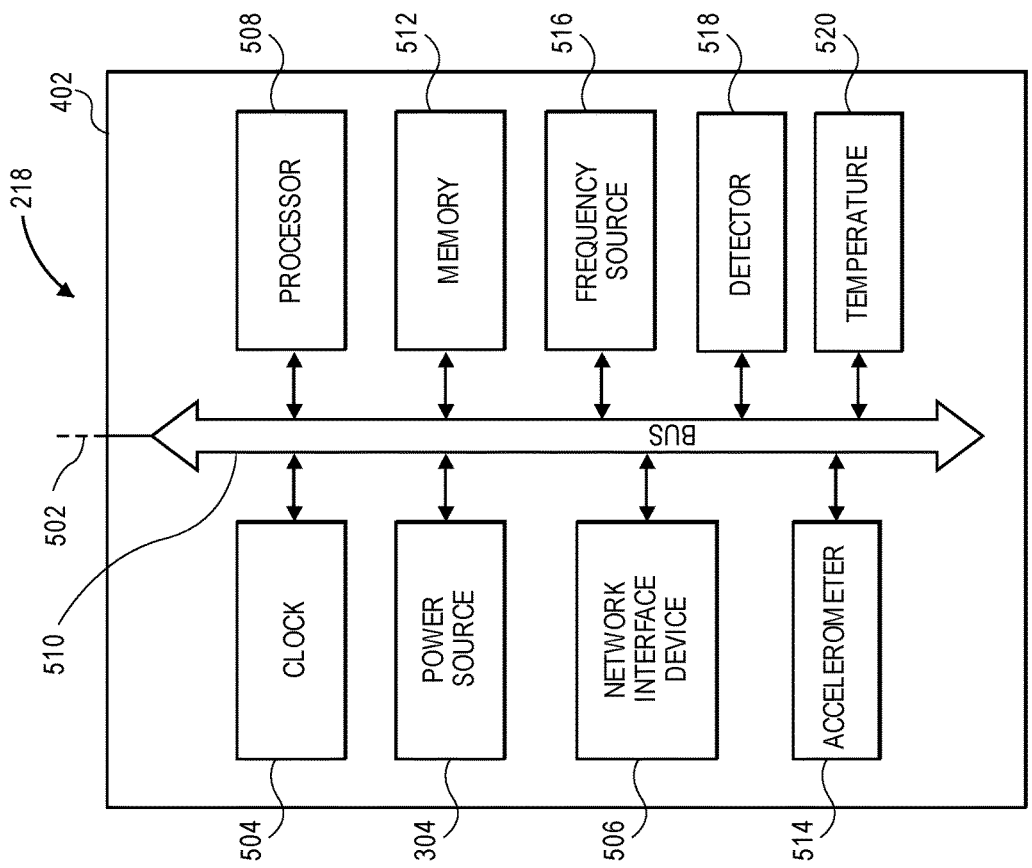
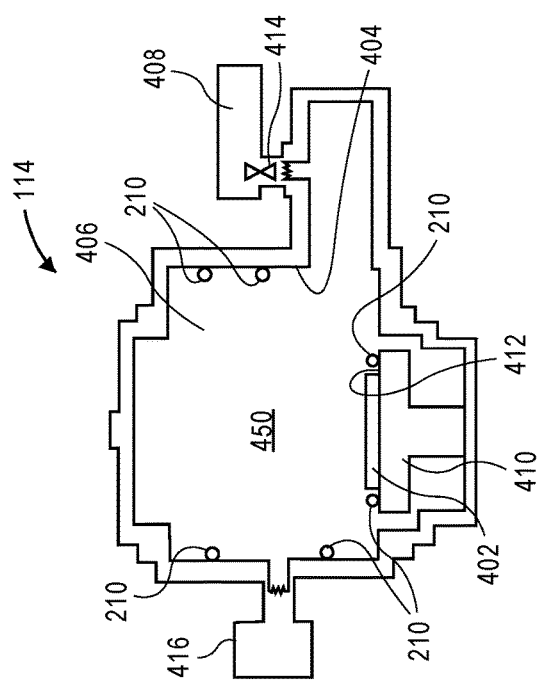
FIG. 5
FIG. 4

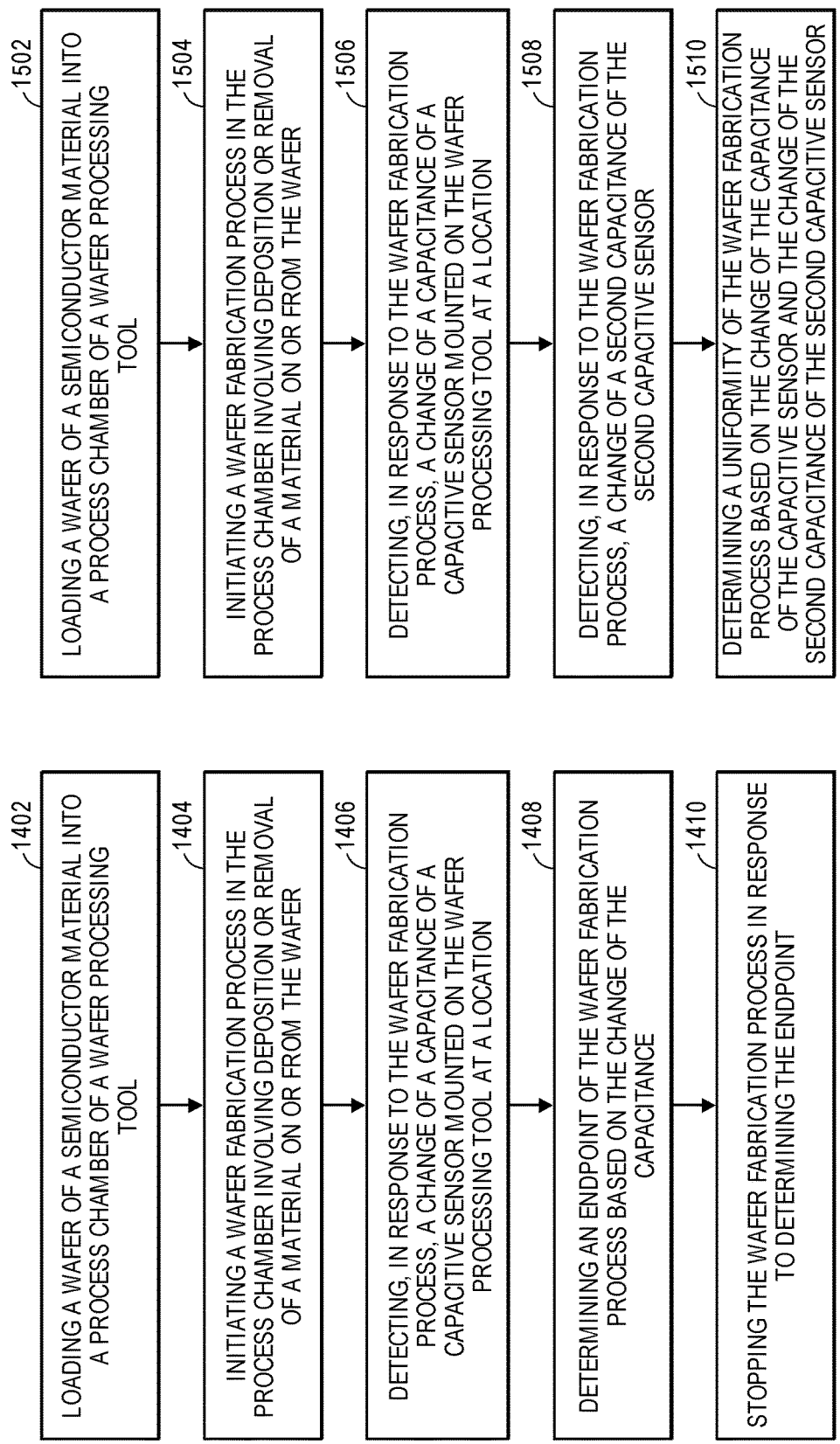

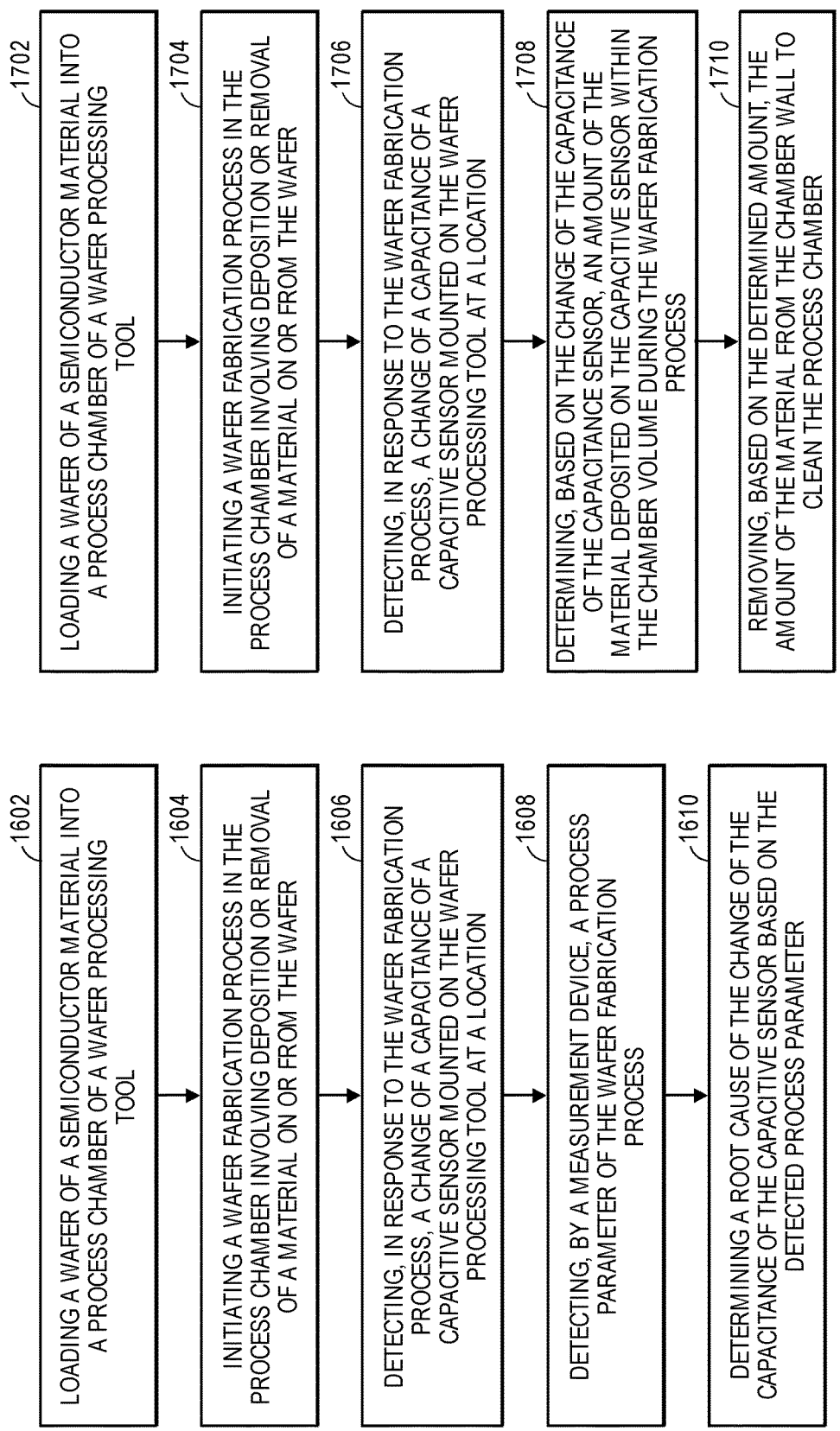

WAFER PROCESSING EQUIPMENT HAVING CAPACITIVE MICRO SENSORS

BACKGROUND

1) Field

Embodiments relate to the field of semiconductor processing and, in particular, to devices and methods for monitoring and control of wafer fabrication processes and equipment.

2) Description of Related Art

A primary concern in the manufacture of semiconductor devices is particle contamination of a semiconductor wafer. Such contamination typically occurs during one or more operations performed by a wafer processing tool during manufacture of the semiconductor devices. For example, the wafer processing tool may include several interfaces, e.g., several chambers interconnected by load locks, and the actuation or operation of any of these system components may generate metallic or nonmetallic particles such as aluminum, stainless steel, zirconium, or other particles that can contaminate a semiconductor wafer in the tool. One skilled in the art will appreciate that particles may come from many sources within the wafer processing tool other than interfaces and moving parts, and thus, the above is provided by way of example.

To identify a source and/or root cause of particle contamination, semiconductor wafers are periodically processed through one or more chambers of the wafer processing tool and then subjected to a particle inspection operation. The particle inspection operation requires the processed wafer to be queued for inspection by optical inspection equipment to identify a location and general size of particles, and then queued for inspection by scanning electron microscopy, energy dispersive spectroscopy, or other inspection techniques to determine a presence and/or composition of particles on the wafer. After detecting the presence and composition of the particles, additional troubleshooting may be required to identify which of the operations performed by the wafer processing tool actually led to the particle contamination.

The manufacture of semiconductor devices may involve the deposition and removal of material, and more particularly semiconductor material, on a substrate by the wafer processing tool using, e.g., deposition or etching processes. To accurately deposit or remove a specified amount of semiconductor material, film thickness measurement techniques may be used. For example, material deposition and material removal rates may be indirectly measured by processing a wafer of semiconductor material for a given amount of time, and then measuring an amount of film deposited or removed using an ellipsometer. Furthermore, sensors have been used to measure secondary factors that correlate with deposition/removal rates to indirectly estimate deposition/removal rates during a wafer fabrication process.

SUMMARY

Embodiments include a particle monitoring device to detect particles within a wafer processing tool. In an embodiment, the particle monitoring device includes a wafer substrate having wafer electronics and a support surface, and a capacitive micro sensor mounted on the support surface at a location. Indeed, several, e.g., many thousands, of sensors may be distributed over a substantial portion of the support surface. The capacitive micro sensor may have a capacitance, and the capacitance may change when a material is deposited on or removed from the capacitive micro sensor.

The particle monitoring device may include a pair of conductors, e.g., a first conductor having first elongated conductors, and a second conductor having second elongated conductors interdigitated with the first elongated conductors. The capacitive micro sensor may include a coating over one or more of the conductors. In an embodiment, the coating includes the material that is removed from capacitive micro sensor to change the capacitance. In an embodiment, the coating includes surface area increasing structures, e.g., pores, within which the material is deposited to change the capacitance.

The particle monitoring device may be fabricated to have a wafer form factor and a laminate structure. For example, a barrier layer may be between the capacitive micro sensor and the wafer substrate. The particle monitoring device may include electrical interconnects, e.g., through silicon vias, connecting the wafer electronics to the capacitive micro sensors through the barrier layer. Accordingly, the capacitive micro sensors may be stripped by a plasma or chemical process above the barrier layer, and the wafer electronics may be protected from the plasma or chemical process under the barrier layer. The wafer electronics may include a processor operably coupled to the capacitive micro sensor to record the location of the capacitive micro sensor when the capacitance changes, and the processor may be powered by a power source encapsulated and protected between a top layer, a bottom layer, and a barrier seal of the particle monitoring device laminate structure.

Embodiments include a wafer processing tool having a capacitive micro sensor to monitor or control a wafer fabrication process, e.g., material deposition or removal. In an embodiment, the wafer processing tool includes a chamber wall around a chamber volume, and a capacitive micro sensor may be mounted on the wafer processing tool at any location. For example, the capacitive micro sensor may be mounted in proximity to one or more of the chamber wall, a lift pin, a load lock, a gas line, a robot, or a pressure control valve of the wafer processing tool. A capacitance of the capacitive micro sensor may change in response to the wafer fabrication process at any of those locations, and the capacitance change may be measured to monitor or control the wafer fabrication process, or to signal a need for repair of the wafer processing tool.

The wafer processing tool having a capacitive micro sensor may be used for various methods. For example, a wafer fabrication process performed by the wafer processing tool may be controlled based on a detected change in the capacitance of the capacitive micro sensor. The controlling may include endpointing the wafer fabrication process. The controlling may include ensuring a rate for the wafer fabrication process. The controlling may include determining a uniformity of the wafer fabrication process. The controlling may include determining a root cause of the capacitance change. The controlling may include removing an amount of material from the chamber wall. The controlling may include measuring a DC bias of a wafer.

The above summary does not include an exhaustive list of all aspects. It is contemplated that all systems and methods are included that can be practiced from all suitable combinations of the various aspects summarized above, as well as those disclosed in the Detailed Description below and particularly pointed out in the claims filed with the application.

Such combinations have particular advantages not specifically recited in the above summary.

BRIEF DESCRIPTION OF THE DRAWINGS

FIG. 4 is a sectional illustration of several capacitive micro sensors mounted on a wafer processing tool, in accordance with an embodiment.

FIG. 5 is an illustration of a block diagram of electronic circuitry of a particle monitoring device or a wafer processing tool, in accordance with an embodiment.

FIG. 14 is an illustration of a flowchart representing operations in a method of endpointing a wafer fabrication process, in accordance with an embodiment.

FIG. 15 is an illustration of a flowchart representing operations in a method of determining a uniformity of a wafer fabrication process, in accordance with an embodiment.

FIG. 16 is an illustration of a flowchart representing operations in a method of determining a root cause of a change of a wafer fabrication process, in accordance with an embodiment.

FIG. 17 is an illustration of a flowchart representing operations in a method of extending a lifetime of a capacitive micro sensor, in accordance with an embodiment.

DETAILED DESCRIPTION

Figure 1:
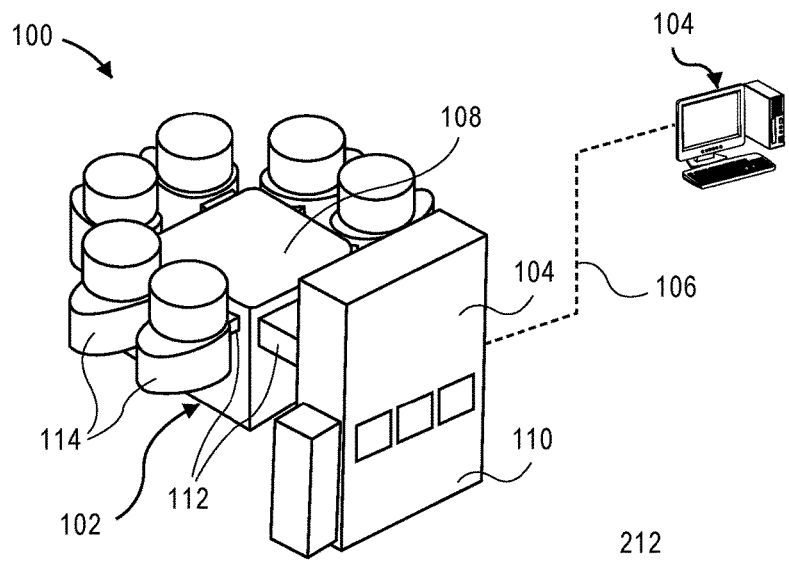
FIG. 1 is an illustration of a wafer processing system, in accordance with an embodiment.

Devices and methods used for particle detection, etch/deposition rate monitoring, or other manufacturing or control of a wafer fabrication process, are described in accordance with various embodiments. In the following description, numerous specific details are set forth in order to provide a thorough understanding of embodiments. It will be apparent to one skilled in the art that embodiments may be practiced without these specific details. In other instances, well-known aspects are not described in detail in order to not unnecessarily obscure embodiments. Furthermore, it is to be understood that the various embodiments shown in the accompanying drawings are illustrative representations and are not necessarily drawn to scale.

Existing techniques for identifying the presence, composition, or source of particle contamination in a semiconductor wafer are time-consuming, expensive, and difficult. Distances between a wafer processing tool and defect inspection equipment, as well as work queues for the inspection equipment, can mean that the inspection process takes an hour or more, delaying mean time to repair the wafer processing tool. The inspection equipment is also expensive, costing in the range of several million dollars to buy, and requiring fabrication facility space for non-value-added wafer inspection equipment. Furthermore, the troubleshooting process used to identify the exact operation that caused the particle contamination is tedious to perform, and uses numerous wafers costing more than a hundred dollars each.

In an aspect, a particle monitoring device allows for system-level particle detection in a wafer processing tool at all pressure regimes. The particle monitoring device may include numerous micro sensors, e.g., capacitive micro sensors, built into a wafer form factor such that the particle monitoring device can be moved between chambers of the wafer processing tool and can be subjected to the same process operations as would be a semiconductor wafer. Thus, the particle monitoring device may collect real-time information about the precise time when (and the precise location where) a particle lands on the wafer-like device during the wafer fabrication process, including during process operations performed under vacuum conditions. Accordingly, a source and root cause of particle contamination may be determined quickly and without the need for expensive inspection equipment or tedious troubleshooting. Such quick determination can reduce mean time to repair the wafer processing tool, or can reduce time to qualify the wafer processing tool for production. Furthermore, the particle monitoring device can replace costly defect inspection equipment and free up fabrication facility space for value-added wafer processing equipment.

Existing techniques for monitoring material deposition or removal of a wafer fabrication process either do not provide real-time measurement and control of the wafer fabrication process, or provide an estimate of material deposition/removal based on correlation to a secondary factor rather than measuring the deposition/removal directly. For example, an ellipsometer may be used to measure film thickness, however, since the ellipsometer is a periodic monitor, the ellipsometer cannot detect real-time excursions or drifts in the deposition/removal rate for normal production runs. Furthermore, sensors installed in a process chamber of a wafer processing tool to measure secondary factors, such as RF match positions or gas concentrations in a plasma, do not directly measure the variable of concern (deposition/removal rates) and such measurements become more challenging in chambers that do not have a plasma.

In an aspect, a wafer processing system includes a micro sensor, e.g., a capacitive micro sensor, mounted at a location on a wafer processing tool to measure material deposition or material removal in all pressure regimes, e.g., under vacuum conditions, and under plasma-less conditions. The capacitive micro sensor mounted on the process chamber may include a capacitance, and the capacitance may change when material is deposited on or removed from a sensor surface, e.g., a coating. Thus, real-time measurement of material deposition or removal amounts or rates, as well as uniformity of such amounts or rates, may be monitored and used to control a wafer fabrication process performed by the wafer processing system.

It will be understood that the wafer processing systems and methods described below could be used in any form factor or process where materials are deposited or removed from a substrate. More particularly, although the wafer processing systems and methods are described with respect to wafer processing for the fabrication of integrated circuits, the devices and methods may also be adapted for use in other technologies, such as displays in the electronics industry and/or photovoltaic cells in the solar industry. It will also be appreciated that the equipment configurations, e.g., capacitive micro sensors mounted at various locations within a wafer processing tool, may be used to detect process parameters other than particle presence or deposition/removal rates. For example, capacitive micro sensors may be used to detect a DC bias of a wafer in the wafer processing tool, as described below. Accordingly, a wafer processing tool having capacitive micro sensors may find wide application within wafer fabrication tools and process.

Referring to FIG. 1, an illustration of a wafer processing system is shown in accordance with an embodiment. A wafer processing system 100 may include a wafer processing tool 102 communicatively coupled to a computer system 104 by a communication link 106. Communication link 106 may be a wired or wireless connection, i.e., wafer processing tool 102 may communicate directly or wirelessly with computer system 104. It will be appreciated that although data may be transferred from wafer processing tool 102 and/or a device within wafer processing tool 102 by communication link 106, in some embodiments, the device within wafer processing tool 102 may be a passive device. That is, the device may be processed by wafer processing tool 102, and may undergo a change, and the change may be measured after the device is taken out of wafer processing tool 102. This may be a feature of, for example, of a particle detection tool or an etch/deposition monitoring tool, as described below.

Wafer processing tool 102 may include a buffer chamber 108 physically connected to a factory interface 110 by one or more load locks 112. Furthermore, one or more process chambers 114 may be physically connected to buffer chamber 108 by one or more respective load locks 112. Buffer chamber 108 may act as an intermediate volume, larger than respective volumes of process chambers 114, that remains at a low pressure, albeit at a pressure higher than the process pressures within process chambers 114. Thus, a semiconductor wafer, e.g., a silicon wafer, may be moved between chambers of wafer processing tool 102 under vacuum conditions during the manufacture of semiconductor devices. Such movement may be enabled by various devices included in the wafer processing tool 102, e.g., robots, robotic arms, shuttles, etc.

Various manufacturing operations may be performed in process chambers 114. For example, at least one process chamber 114 may be an etch chamber, a deposition chamber, a chamber of a semiconductor lithography tool, or any other semiconductor process chamber. As such, process chamber 114 may be used to perform wafer fabrication processes under vacuum conditions, atmospheric conditions, or any other pressure regime.

In addition to varying pressure regimes, process chambers 114 may also be used to perform manufacturing processes having different energetic conditions. For example, process chamber 114 may be a radical-driven etch chamber or a deposition chamber that does not include a plasma. That is, process chamber 114 may be plasma-less during a wafer fabrication process.

During a wafer fabrication process, a semiconductor wafer may be transferred from buffer chamber 108 into one of the process chambers 114 through load lock 112. Process chambers 114 may have a chamber pressure that is lowered, e.g., using a vacuum pump and/or turbo pump (FIG. 4), to a vacuum condition. In the context of this description, a vacuum condition may be any pressure less than 0.5 atm. In an embodiment, the vacuum condition in process chamber 114 exists when process chamber 114 has a chamber pressure less than the pressure of buffer chamber 108, e.g., less than 100 millitorr. Accordingly, a manufacturing operation performed in process chamber 114 may be carried out under vacuum conditions.

One or more particles may be generated during the manufacturing operation performed in process chamber 114. For example, a particle may be a metallic or nonmetallic particle that is emitted into process chamber 114 when a specific operation occurs, e.g., when a valve of load lock 112 is opened, when a load lock door is locked, when lift pins are moving, or when any other tool operation occurs. The emitted particles may land on the semiconductor wafer, and a landing location and time of particle may correspond to a source of the particle contamination. For example, a particle may land on a semiconductor wafer nearer to load lock 112 and at a time when load lock 112 is closed, indicating that a component of load lock 112 and/or the actuation of load lock 112 is the source of the particle. Thus, it can be seen that particle monitoring that provides information about a location and a time when the particle lands on the semiconductor wafer may be useful in determining a source of particle contamination.

Figure 2:
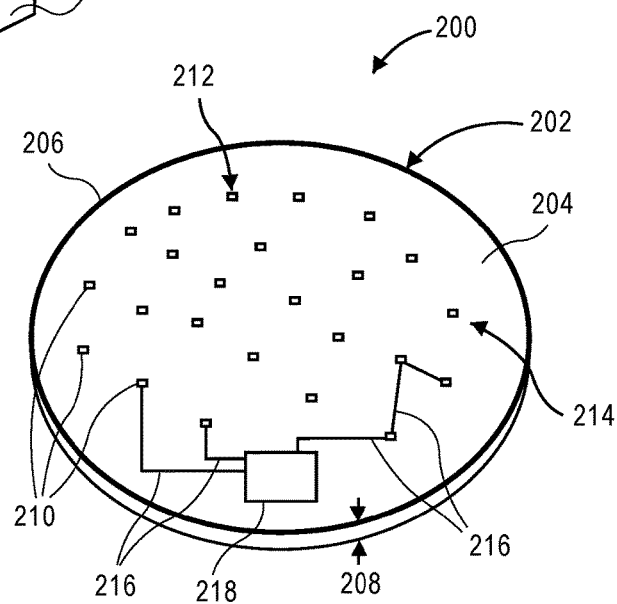
FIG. 2 is an illustration of a particle monitoring device, in accordance with an embodiment.

Referring to FIG. 2, an illustration of a particle monitoring device is shown in accordance with an embodiment. Particle monitoring device 200 may be configured to be moved between chambers, e.g., buffer chamber 108 and/or process chambers 114, of wafer processing tool 102. For example, particle monitoring device 200 may include a wafer substrate 202 having an overall form factor and/or a same material and shape as a semiconductor wafer. That is, wafer substrate 202 may be at least partially composed of a semiconductor material, e.g., a crystalline silicon material. Furthermore, wafer substrate 202 may have a wafer form factor that is essentially disc-shaped and includes a support surface 204 having a diameter 206. Support surface 204 may be an upper surface of the disc, and a bottom surface of wafer substrate 202 (not shown) may be spaced apart from support surface 204 by a thickness 208. In an embodiment, the wafer form factor of wafer substrate 202 includes diameter 206 between 95 to 455 mm, e.g., diameter 206 may nominally be 100 mm, 300 mm, or 450 mm. Furthermore, the wafer form factor of wafer substrate 202 may include thickness 208 less than 1 mm, e.g., 525 µm, 775 µm, or 925 µm. Thickness 208 may also be greater than 1 mm, e.g., several millimeters up to 10 mm. Accordingly, particle monitoring device 200 may be manufactured using readily available wafer materials and typical wafer manufacturing processes and equipment, and may essentially simulate a semiconductor wafer when processed by wafer processing tool 102.

Particle monitoring device 200 may include several micro sensors mounted on support surface 204 at predetermined locations. The micro sensors may be one or more of the micro sensor types described below. In an embodiment, the micro sensors are capacitive micro sensors 210. For example, numerous capacitive micro sensors 210, e.g., thousands to millions of capacitive micro sensors 210, may be built on support surface 204. Each capacitive micro sensor 210 may have a known location. For example, a first capacitive micro sensor 212 may be located at a first location, and a second capacitive micro sensor 214 may be located at a second location. The second location may have a known position relative to the first location, or relative to some other reference point on particle monitoring device 200.

Capacitive micro sensors 210 may be distributed across support surface 204 randomly, or may be arranged in a predetermined pattern. For example, capacitive micro sensors 210 shown in FIG. 2 appear to be randomly distributed across support surface 204, even though their absolute or relative locations may be predetermined and known. In an embodiment, capacitive micro sensors 210 are arranged in a predetermined pattern, e.g., a grid pattern, a concentric circle pattern, a spiral pattern, etc. Such patterns may be achieved using known etching processes to build capacitive micro sensors 210 at precise locations on support surface 204 of particle monitoring device 200.

In an embodiment, capacitive micro sensors 210 are spread over a majority of a surface area of support surface 204. For example, an outer profile drawn through the outermost capacitive micro sensors 210 of the micro sensor array may delineate an array area that is at least half of the surface area of support surface 204. In an embodiment, the array area is at least 75% of the surface area, e.g., greater than 90% of the surface area of support surface 204.

The capacitive micro sensors 210 of particle monitoring device 200 may be interconnected with each other or other circuitry through one or more electrical connector. For example, capacitive micro sensors 210 may be connected in series by an electrical trace 216 running over support surface 204. Alternatively or in addition, several capacitive micro sensors 210 may be electrically connected in parallel by respective electrical traces 216. Thus, electrical connections may be made between capacitive micro sensors 210, or capacitive micro sensors 210 may be connected to wafer electronics, i.e., electronic circuitry 218, using electrical traces, electrical leads, vias, and other known types of electrical connectors.

Each capacitive micro sensor 210 of particle monitoring device 200 may be configured to sense a change in a given parameter when a particle interacts with the sensor. More particularly, a capacitive micro sensor 210 may have a capacitance, and the capacitance may change when a material is deposited on or removed from the capacitive micro sensor 210. Thus, the capacitance may change when the capacitive micro sensor 210 receives the particle within a chamber, e.g., process chamber 114, of wafer processing tool 102. Here, the term "receives" indicates an interaction between particle and capacitive micro sensor 210 that affects the capacitance. It will be appreciated that particle monitoring device 200 may include other micro sensor types, as described below, and thus a different parameter may be sensed when a particle is received by such micro sensors. For example, the parameter may be a voltage, a current, or another physical or electrical characteristic of a micro sensor that changes when the particle lands on the micro sensor, passes near or through the micro sensor, or impacts the micro sensor, as described below. Other particle-sensor interactions will be understood by a skilled artisan when reading this description.

Figure 3:
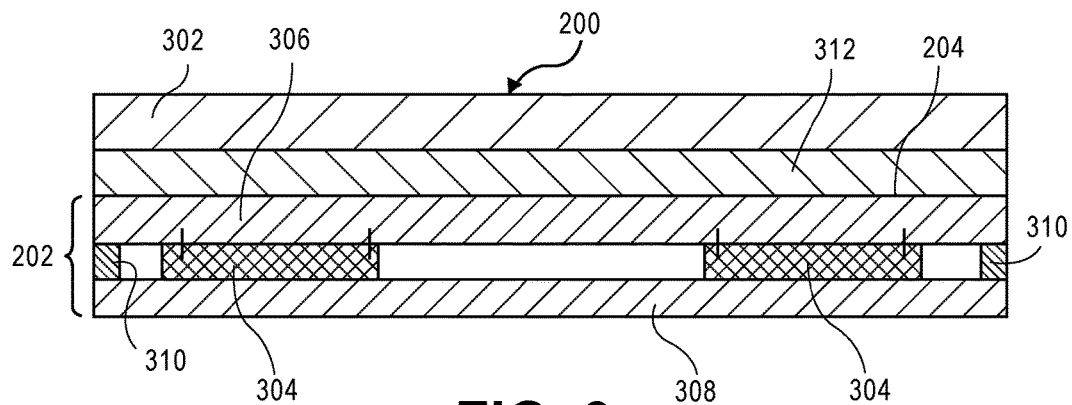
FIG. 3 is a sectional illustration of a particle monitoring device, in accordance with an embodiment.

Referring to FIG. 3, a sectional illustration of a particle monitoring device is shown in accordance with an embodiment. Capacitive micro sensors 210 may be packaged on wafer substrate 202 that can be automatically loaded into and moved throughout the system, similar to loading and processing of a typical semiconductor wafer. Accordingly, capacitive micro sensors 210 can experience the same environment as production semiconductor wafers. In an embodiment, a sensor layer 302 having several capacitive micro sensors 210 covers at least a portion of wafer substrate 202. Thus, capacitive micro sensors 210 of sensor layer 302 are mounted on support surface 204 of wafer substrate 202.

In an embodiment, wafer substrate 202 is structured to protect electronic circuitry 218 of particle monitoring device 200 from attack by a plasma in wafer processing tool 102. As such, wafer substrate 202 may include electronic circuitry 218 sandwiched between a top layer 306 and a bottom layer 308. For example, electronic circuitry 218 may include a power source 304, e.g., a thin-film battery. The thin-film battery may be encapsulated between layers 306, 308 of silicon, and thus, may be protected against plasma attack from a top or bottom by two silicon wafers. Furthermore, power source 304 may be protected against plasma attack from the sides by a barrier seal 310. Barrier seal 310 may be sandwiched between top layer 306 and bottom layer 308 around power source 304. More particularly, barrier seal 310 may extend around a circumference of wafer substrate 202 to form a protective wall surrounding the sides of power source 304. Thus, power source 304 may be encapsulated within wafer substrate 202.

Power source 304 may be electrically connected to one or more components of electronic circuitry 218 in top layer 306 and/or sensor layer 302. For example, electronic circuitry 218, e.g., control electronics such as a processor, a memory, or communication electronics, may be built into top layer 306 of wafer substrate 202. Power source 304 may be connected to electronic circuitry 218 in top layer 306 by electrical connections such as through silicon vias extending through one or more layers of particle monitoring device 200. Similarly, power source 304 and/or electronic circuitry 218 in top layer 306, e.g., the processor, may be electrically connected to capacitive micro sensors 210 in sensor layer 302 by electrical traces or electrical vias. Accordingly, power source 304 may be electrically coupled to a processor of electronic circuitry 218, capacitive micro sensors 210, or other electronic circuitry 218, to power the electronics.

Capacitive micro sensors 210 may be exposed to plasma within wafer processing tool 102, and thus, the sensors may eventually wear out. Accordingly, it may be advantageous to package capacitive micro sensors 210 such that the micro sensors are recyclable. In an embodiment, packaging of capacitive micro sensors 210 includes a barrier layer 312 between capacitive micro sensor 210 and an underlying substrate. For example, in the case of particle monitoring device 200, barrier layer 312 may be disposed between capacitive micro sensor 210 and support surface 204 of wafer substrate 202. Capacitive micro sensor 210 may be electrically connected to wafer electronics, i.e., electronic circuitry 218, through barrier layer 312 using known interconnect technology such as through silicon vias. Barrier layer 312 between the control electronics and the sensors may protect the electronics during recycling. For example, capacitive micro sensor 210 may be removable by stripping agents, i.e., by a plasma, gaseous or a liquid etchant, and barrier layer 312 may not be strippable by the same stripping agent. That is, barrier layer 312 may be any material, conductive or insulating, that is impervious to a stripping agent, such as a gas phase or liquid etchant. Accordingly, once capacitive micro sensors 210 reach an end of their useful life, the plasma 450 may be applied to strip the micro sensors of sensor layer 302 away from barrier layer 312 without degrading electronic circuitry 218 built into wafer substrate 202. Similarly, mechanical stripping may be used to remove the worn-out sensors. A new sensor layer 302 having a new set of capacitive micro sensors 210 may then be formed on barrier layer 312 to refurbish particle monitoring device 200 at a lower cost than forming an entirely new particle monitoring device 200.

Components of particle monitoring device 200 may be formed using known semiconductor processes and techniques. For example, as described above, electrical connections between sensors and electronic circuitry 218 may be formed through barrier layer 312 and/or wafer substrate 202 using through silicon vias. Furthermore, components may be built into layers of particle monitoring device 200 using known techniques. For example, capacitive micro sensor 210 may be formed separately and then mounted on barrier layer 312 using flip chip technology during the recycling process.

Implementation of capacitive micro sensor 210 in particle monitoring device 200 represents an embodiment of using capacitive micro sensors 210 for particle detection. Other uses of capacitive micro sensors 210 in wafer fabrication processing equipment and methods exist. For example, capacitive micro sensors 210 may be mounted on wafer processing tool 102 to detect or measure etch/deposition rate, and such data may be used to control a wafer fabrication process, as described below.

Referring to FIG. 4, a sectional illustration of several capacitive micro sensors mounted on a wafer processing tool is shown in accordance with an embodiment. A wafer 402, e.g., a wafer 402 of semiconductor material or the wafer substrate 202 of particle monitoring device 200, may be subjected to a wafer fabrication process in process chamber 114 of wafer processing tool 102. Wafer 402 may experience different pressure conditions as the wafer 402 moves through wafer processing tool 102. For example, the semiconductor wafer 402 may be inserted into the factory interface 110 at atmospheric conditions. Then, as the semiconductor wafer 402 goes into a load lock 112 between factory interface 110 and buffer chamber 108, the load lock 112 may be brought to a vacuum condition of 120 millitorr. The semiconductor wafer 402 may then pass from the load lock 112 into buffer chamber 108, having a buffer chamber 108 pressure of 100 millitorr.

Wafer 402 may be transferred from buffer chamber 108 into one of the process chambers 114 through load lock 112. For example, process chamber 114 may include a chamber wall 404 around a chamber volume 406, and chamber volume 406 may be sized to receive wafer 402. Thus, semiconductor material may be deposited on or removed from wafer 402 during a wafer fabrication process within process chamber 114. During the wafer fabrication process, chamber volume 406 of process chamber 114 may have a chamber pressure that is lowered to a vacuum condition using, e.g., a vacuum source 408 such as a vacuum pump and/or turbo pump. In the context of this description, a vacuum condition may be any pressure less than 0.5 atm. In an embodiment, the vacuum condition in process chamber 114 exists when process chamber 114 has a chamber pressure less than the pressure of buffer chamber 108, e.g., less than 100 millitorr. Accordingly, the process chamber 114 may be under vacuum conditions during the manufacturing operation of the wafer fabrication process. Furthermore, the vacuum conditions may reduce or eliminate gaseous mixtures from chamber volume 406, and thus, chamber volume 406 may be plasma-less during the wafer fabrication process.

One or more micro sensors, e.g., capacitive micro sensors 210, may be mounted on wafer processing tool 102. For example, capacitive micro sensors 210 may be mounted at one or more locations on process chamber 114 within chamber volume 406. More particularly, several capacitive micro sensors 210 may be mounted at predetermined locations on chamber wall 404 within chamber volume 406.

In an embodiment, capacitive micro sensor(s) 210 are mounted on portions of wafer processing tool 102 other than chamber wall 404. For example, instead of or in addition to having capacitive micro sensors 210 mounted on chamber wall 404, one or more capacitive micro sensors 210 may be mounted on a wafer holder 410 within process chamber 114. Wafer holder 410 may be, for example, an electrostatic chuck having electrode(s) to electrostatically clamp wafer 402 during a wafer fabrication process. Wafer holder 410 may include a holding surface 412 upon which wafer 402 is clamped. For example, holding surface 412 may be a layer of dielectric material over wafer holder 410, and capacitive micro sensor 210 may be mounted on holding surface 412. More particularly, capacitive micro sensors 210 may be mounted on holding surface 412 in a region near and/or laterally offset from wafer 402 during the wafer fabrication process. For example, a process kit may include a ring around wafer 402 on holding surface 412, and capacitive micro sensor 210 may be mounted on process kit.

It is contemplated that capacitive micro sensors 210 may be located in process chamber 114 or built into consumable or non-consumable parts of process chamber 114, e.g., wafer holder 410, within close enough proximity to wafer 402 to detect changes in material deposition or removal rates of wafer 402. For example, wafer 402 may have a forward-facing surface, i.e., a surface facing away from holding surface 412 toward a plasma 450, and capacitive micro sensor 210 may be mounted on holding surface 412 such that a sensor surface sensitive to material deposition/removal is also facing forward.

It will be appreciated that capacitive micro sensors 210 may be mounted at locations on wafer processing tool 102 other than locations within process chamber 114. For example, one or more capacitive micro sensors may be mounted on, in, or in proximity to, load lock 112. Similarly, capacitive micro sensor 210 may be mounted on, in, or in proximity to a gas line (not shown) of wafer processing tool 102, a pressure control valve 414 of wafer processing tool 102 that controls flow to vacuum source 408, a robot of wafer processing tool 102, or a lift pin of wafer processing tool 102, to name several example locations. Capacitive micro sensors 210 may be mounted in proximity to other locations of wafer processing tool 102 depending on the particular process measurement and control that is desired. Here, "in proximity to" is used as a relative term, but it will be appreciated that the presence of capacitive micro sensor 210 near a particular component of wafer processing tool 102 is intended to describe a distance such that particles or material deposited on or removed from the component is statistically likely to interact with the mounted sensor. Examples of these interactions are described further with respect to the methods described below.

As used herein, the term "micro" may refer to the descriptive size of certain sensors or structures in accordance with embodiments. For example, the term "capacitive micro sensor" may refer to a capacitive sensor having dimensions on the scale of nanometers to 100 µm. That is, in an embodiment, capacitive micro sensors 210 as described below may have typical dimensions in the range of 0.05 to 100 µm for individual cells which may be connected in parallel or series. Accordingly, capacitive micro sensors 210 as described herein are readily distinguishable from other sensor types, e.g., microbalances, which are instruments capable of making precise measurements of weight on the order of a million parts of a gram. That is, microbalances may measure weight on a micro-scale, but are not within the same size range of the micro sensors described herein. The difference in size range is advantageous at least because several micro sensors, e.g., thousands, may be fit into chamber volume 406 or elsewhere on wafer processing tool 102, whereas several microbalances may not fit into chamber volume 406 that is sized to receive a semiconductor wafer 402.

As used herein, the term "micro sensors" may also refer to sensors that are fabricated using materials and manufacturing processes pertinent to microelectromechanical systems (MEMS). That is, capacitive micro sensors 210 described herein may be fabricated using MEMS processes such as deposition processes, patterning, etching, etc. Accordingly, capacitive micro sensors 210 may be MEMS-scale sensors having a size and structure formed using MEMS processes. It is to be appreciated, however, that embodiments are not necessarily so limited, and that certain aspects of the embodiments may be applicable to larger, and possibly smaller size scales.

While as few as one micro sensor may be mounted on wafer processing tool 102, numerous micro sensors, e.g., hundreds to millions of micro sensors, may be fit into chamber volume 406 or mounted elsewhere on wafer processing tool 102. That is, given the MEMS-scale size of micro sensors described below, many micro sensors may be distributed along wafer processing tool 102, e.g., around chamber wall 404 (or other components of wafer processing tool 102), to monitor wafer fabrication process parameters, e.g., a deposition/removal of semiconductor material within process chamber 114, in real-time.

Each capacitive micro sensor 210 may have a known location. For example, a first capacitive micro sensor may be located at a first predetermined location on wafer processing tool 102, e.g., at a first location within chamber volume 406, and a second capacitive micro sensor may be located at a second predetermined location on wafer processing tool 102, e.g., at a second location within chamber volume 406. Capacitive micro sensors 210 may be distributed on process chamber 114 randomly or in a predetermined pattern. For example, the second location may have a known position relative to the first location, or relative to some other reference point on process chamber 114. Thus, uniformity of material deposition/removal may be determined as described below, by comparing real-time measurements from the first capacitive micro sensor and the second capacitive micro sensor.

Wafer processing tool 102 may include other sensors and/or measurement instruments to detect a process parameter of the wafer fabrication process. The other sensors and/or measurement instruments may not be micro sensors. For example, in contrast to MEMS-scale sensors described below, wafer processing tool 102 may include an optical spectrometer 416 mounted on process chamber 114 or otherwise mounted to detect an optical emissions spectrometry (OES) signature of chamber volume 406 during the wafer fabrication process. The OES signature may identify a type and amount of elements within chamber volume 406. For example, the OES signature may identify what chemical elements are present in a plasma 450 within chamber volume 406 during the wafer fabrication process. Other sensors may be used to detect other process parameters of the wafer fabrication process performed in chamber volume 406. Such other sensors may include electrical sensors to measure power delivered to process chamber 114 or wafer 402, electrical sensors to measure electrical characteristics of wafer holder 410, etc. Such sensors may not measure an actual amount or rate of deposition/removal of semiconductor material 808, but may nonetheless be correlated to actual deposition/removal measurements made by capacitive micro sensors 210 for the reasons described below.

Other sensors may also be used to gather information that correlates to a presence of a particle in wafer processing tool 102. For example, one or more measurement devices, e.g., accelerometers (not shown), may be mounted on moving parts of wafer processing tool 102. In an embodiment, a robot or a robotic arm includes an accelerometer to sense motion of the robot. Alternatively, a load lock door includes an accelerometer. Accordingly, a process parameter of a wafer fabrication process, e.g., motion data representative of a robotic movement, may be detected by the accelerometer and may be correlated to particle sensing data gathered from capacitive micro sensor 210 to determine a source of particulate. Applications of such other sensors, e.g., accelerometers, are described further below.

Capacitive micro sensors 210 and/or measurement instruments or devices of wafer processing tool 102 may be interconnected with each other or other circuitry through one or more electrical connector. For example, capacitive micro sensors 210 may be connected in series by an electrical trace running over chamber wall 404 and/or wafer holder 410. Alternatively or in addition, several capacitive micro sensors 210 may be electrically connected in parallel by respective electrical traces 216. Thus, electrical connections may be made between capacitive micro sensors 210 and/or capacitive micro sensors 210 may be connected to electronic circuitry 218, using electrical traces, electrical leads, vias, and other known types of electrical connectors.

Referring to FIG. 5, an illustration of a block diagram of electronic circuitry of a particle monitoring device or a wafer processing tool is shown in accordance with an embodiment. Electronic circuitry 218 of particle monitoring device 200 or wafer processing tool 102 may be supported by an underlying structure of a wafer 402 or wafer processing tool 102. For example, electronic circuitry 218 may be mounted on top layer 306 of particle monitoring device 200, as described above. Electronic circuitry 218 may be enclosed in a housing. The housing and/or electronic components of electronic circuitry 218 may be integral to wafer 402, e.g., the housing may be layers of wafer substrate encapsulating electronic circuitry 218. Alternatively, the housing may be mounted on wafer processing tool 102, e.g., on chamber wall 404 or wafer holder 410. Similarly, the housing may be mounted on another portion of wafer processing tool 102, e.g., on an external surface outside of chamber volume 406. Accordingly, electronic circuitry 218 may be co-located or remotely placed relative to capacitive micro sensor 210. Electronic circuitry 218 may nonetheless be placed in electrical connection with capacitive micro sensor 210 through one or more input/output (I/O) connection 502, e.g., an electrical trace, electrical lead, or via, even when mounted remotely relative to capacitive micro sensor 210.

Electronic circuitry 218 of wafer processing tool 102 may include a clock 504. Clock 504 may be an electronic circuit having an electronic oscillator, e.g., a quartz crystal, to output an electrical signal having a precise frequency, as is known in the art. Thus, clock 504 may be configured to output a time value corresponding to an electrical signal received through I/O connection 502. The time value may be an absolute time value independent of other operations, or the time value may be synchronized to other clocks in wafer processing tool 102. For example, clock 504 may be synchronized to a system clock of wafer processing tool 102, or a system clock of a host computer of a fabrication facility linked to wafer processing tool 102, such that the time value output by clock 504 corresponds to a system time value and/or system operations that are output or controlled by the system clock. Clock 504 may be configured to initiate the output of the time value when a particular process operation occurs. Electronic circuitry 218 of wafer processing tool 102 may include a network interface device 506 to transmit and receive communications between wafer processing tool 102 and the host computer.

Electronic circuitry 218 of wafer processing tool 102 may include a processor 508. Processor 508 may be operably coupled, e.g., electrically connected by a bus 510 and/or traces, to clock 504. Processor 508 represents one or more general-purpose processing devices such as a microprocessor, central processing unit, or the like. More particularly, processor 508 may be a complex instruction set computing (CISC) microprocessor, reduced instruction set computing (RISC) microprocessor, very long instruction word (VLIW) microprocessor, a processor implementing other instruction sets, or processors implementing a combination of instruction sets. Processor 508 may also be one or more special-purpose processing devices such as an application specific integrated circuit (ASIC), a field programmable gate array (FPGA), a digital signal processor (DSP), network processor, or the like.

Processor 508 is configured to execute processing logic for performing the operations described herein. For example, processor 508 may be configured to receive and analyze input signals from several capacitive micro sensors 210 located at different predetermined locations on particle monitoring device 200 or wafer processing tool 102. Accordingly, processor 508 may determine and record data related to the capacitive micro sensors 210 to which it is operably connected. For example, processor 508 may record a location of a capacitive micro sensor 210 when the capacitance of micro sensor changes. Processor 508 may also receive time value outputs from clock 504 corresponding to each received input signal and may record the time value output to memory as a time stamp. Accordingly, processor 508 may compare input signals from several capacitive micro sensors 210, e.g., to determine a uniformity of a wafer fabrication process at a given time. Processor 508 may be configured to determine other types of information based on signals received from capacitive micro sensors 210. For example, input signals received from one or more capacitive micro sensors 210 may be used to endpoint the wafer fabrication process or to determine a root cause of a change in the wafer fabrication process, as described below.

Other functionality may be provided by processor 508 as described herein. For example, processor 508 may include signal processing functionality, e.g., may convert analog signals from capacitive micro sensor 210 into digital signals. Of course, a dedicated digital-to-analog converter may be used for such purposes as well. Similarly, other electronics may be used for any of the processing functions described, such as filtering displacement currents, performing tasks to make logical determinations on data, such as referencing lookup tables, applying correction factors, etc. It will also be appreciated that such processing may be performed in a local or distributed fashion, as is known. Accordingly, such electronics and processing techniques are not discussed at length here in the interest of brevity.

Monitoring of capacitive micro sensors 210 may be performed by processor 508 on an individual or group basis. That is, processor 508 may monitor and record individual data for each capacitive micro sensor 210. Accordingly, each capacitive micro sensor 210 may be individually identifiable, e.g., by a unique sensor identification number that is associated with location or other sensor-specific data. In an embodiment, capacitive micro sensors 210 may be monitored in groups. For example, processor 508 may monitor and record bank data for a group of one or more capacitive micro sensors 210. These groups may be referred to as sensor blocks, and each sensor block may have a corresponding power source and processor. That is, the sensor blocks may function independently from each other and be monitored or controlled separately. Accordingly, the group of capacitive micro sensors 210 may be associated with location or other group-specific data that corresponds to the group of sensors as a whole.

Electronic circuitry 218 of wafer processing tool 102 may include a memory 512 mounted on, e.g., wafer substrate 202 or chamber wall 404. Memory 512 may include one or more of a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), or a secondary memory (e.g., a data storage device). Processor 508 may communicate with memory 512 via bus 510 or other electrical connection. Thus, processor 508 may be operably coupled to memory 512 to record the predetermined location of the triggered capacitive micro sensor 210 and the time value output by clock 504, in the memory 512. That is, memory 512 may log a time when a particle or material is deposited on or removed from capacitive micro sensor 210, and a location where the affected micro sensor is mounted when the material alights on or from the capacitive micro sensor 210.

Electronic circuitry 218 of wafer processing tool 102 may include power source 304, as described above. Power source 304 may include a battery, a capacitor bank, or another known power supply. Power source 304 may be electrically connected to, and may power, one or more of the components of electronic circuitry 218 through bus 510, e.g., capacitive micro sensors 210, clock 504, processor 508, or memory 512.

Electronic circuitry 218 of wafer processing tool 102 may include additional components. For example, electronic circuitry 218 may include an accelerometer 514 that triggers clock 504 to begin outputting a time value when particle monitoring device 200 ceases movement, e.g., after being loaded into a particular process chamber 114 of wafer processing tool 102. Thus, the time value may provide information about when particle monitoring device 200 is loaded into a particular processing station of wafer processing tool 102. Electronic circuitry 218 may include a frequency source 516, e.g., a broad frequency source 516, or a detector 518. Frequency source 516 and detector 518 may have particular application in relation to specific embodiments of capacitive micro sensors 210 of wafer processing tool 102. For example, frequency source 516 and detector 518 may be used to drive and monitor a micro-resonator type micro sensor, as described below.

The components of electronic circuitry 218 described above are illustrative of a range of sensors that may be used, and not restrictive. For example, additional sensors, such as a temperature sensor 520, may be integrated in the fabrication of wafer processing tool 102. Temperatures sensor 520 may monitor a temperature of one or more components of wafer processing tool 102, e.g., chamber volume 406. Various embodiments of capacitive micro sensors 210 are now described. It is stated at the outset that the configurations and illustrations of capacitive micro sensors 210 are illustrative in nature, and many additional configurations may be contemplated by one skilled in the art based on this description.

Figure 6:
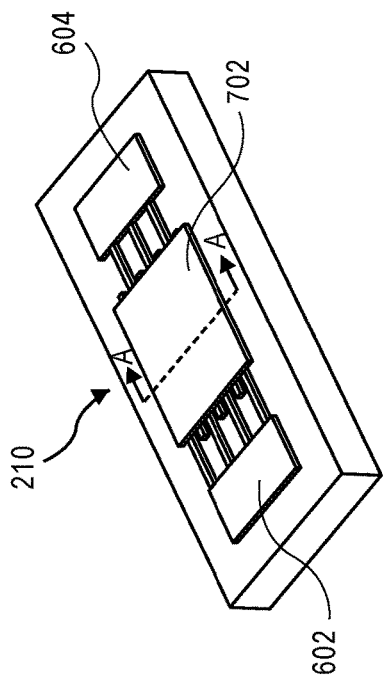
FIG. 6 is a perspective illustration of a capacitive micro sensor of a wafer processing system, in accordance with an embodiment.

Referring to FIG. 6, a perspective illustration of a capacitive micro sensor of a wafer processing system is shown in accordance with an embodiment.

Capacitive micro sensor 210 may have a capacitance, and the capacitance of capacitive micro sensor 210 may change in response to a wafer fabrication process performed by wafer processing tool 102. Capacitive micro sensor 210 may employ two or more electrodes connected to a measurement circuit. For example, capacitive micro sensor 210 may have a pair of conductors that includes a first conductor 602 separated from a second conductor 604 by a dielectric gap. First conductor 602 and/or second conductor 604 may be electrically charged. For example, one or more of the electrodes may be tied directly to drive and sense signals from a measurement circuit of electronic circuitry 218. In an embodiment, one of the electrodes is connected to ground potential.

First conductor 602 and second conductor 604 may be formed from a conductive material, e.g., polysilicon, aluminum, tungsten, etc. The conductors may be formed or otherwise mounted on substrate 606. Substrate 606 may be a portion of wafer substrate 202 of particle monitoring device 200. Alternatively, substrate 606 may be mounted on wafer processing tool 102. Substrate 606 may be a silicon wafer substrate, an organic material, a blanket glass substrate, or another solid dielectric substrate, e.g., alumina, quartz, silica, etc.

Each conductor may include several fingerlike conductors extending from conductive pads 608 along respective planes. For example, first conductor 602 may include several first elongated conductors 610, and second elongated conductor 612 may include several second elongated conductors 612. In an embodiment, first elongated conductors 610 and second elongated conductors 612 are interdigitated. More particularly, the elongated conductors may be interlocked or intermeshed within a same plane to form a capacitance between the fingerlike structures. Signals may be carried in and out of the elongated conductors through conductive pads 608. Accordingly, capacitive micro sensor 210 may include a capacitor having a planar configuration.

Capacitive micro sensor 210 may be designed to maximize sensitivity. For example, the electrodes of capacitive micro sensor 210 may be formed in a small size and separated by a small space. This size scaling can achieve high sensitivity and active area density by making the sensors individually, and as a whole, sensitive to smaller particles and able to detect particles more discretely. By way of example, each elongated conductor may be separated by a dielectric gap distance of less than 3 microns. In some embodiment, the dielectric gap distance may be in a range of 50-100 nm. Accordingly, capacitive micro sensor 210 may detect small perturbations in the dielectric properties between the electrodes. The design of the monitoring and control electronic circuitry 218 may also be manipulated to modulate sensitivity. Accordingly, typical detection ranges of the capacitive micro sensors 210 may be in the low femtofarad to tens of picofarad range, and a resolution of the detection may be on the order of attofarads.

Figure 7:
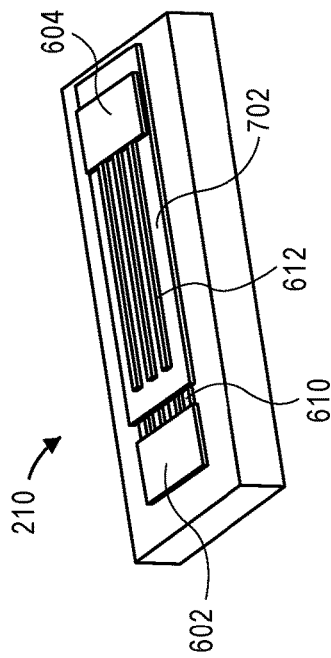
FIG. 7 is a perspective illustration of a capacitive micro sensor of a wafer processing system, in accordance with an embodiment.

Referring to FIG. 7, a perspective illustration of a capacitive micro sensor of a wafer processing system is shown in accordance with an embodiment. Capacitive micro sensor 210 may include a coating 702 over one or more of first conductor 602 or second conductor 604. For example, coating 702 may be applied over a region of the conductors that has been patterned into a planar interdigitated capacitor. Coating 702 may be an organic or dielectric material. More particularly, coating 702 may include a material selected to react to a wafer fabrication process. For example, coating 702 may include a target material of an etching process. In an embodiment, coating 702 includes a dielectric material, such as silicon oxide or silicon nitride. Accordingly, when the etch process is performed by wafer processing tool 102, an amount of coating 702 may be removed.

Figure 8:
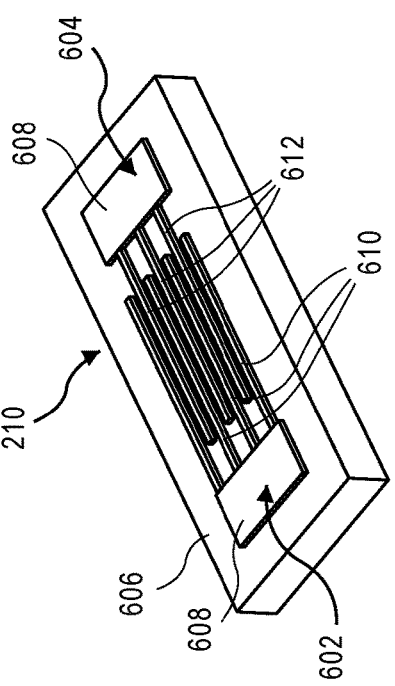
FIG. 8 is a sectional illustration, taken about line A-A of FIG. 7, of a capacitive micro sensor of a wafer processing system, in accordance with an embodiment.

Referring to FIG. 8, a sectional illustration, taken about line A-A of FIG. 7, of a capacitive micro sensor of a wafer processing system is shown in accordance with an embodiment. Capacitive micro sensor 210 includes a pair of conductors 802 over substrate 606. Pair of conductors 802 may, for example, include a first elongated conductor 610 of first conductor 602, and a second elongated conductor 612 of second conductor 604. As described above, pair of conductors 802 may be covered at least in part by coating 702. Coating 702 may be a blanket coating as shown in FIG. 7. More particularly, coating 702 may include a filler portion 804 laterally between the interdigitated conductors, i.e., filling the dielectric gap, and an overcoat portion 806 layered over a top surface of the conductors. Coating 702 may have a laminated structure, e.g., filler 804 may be a first layer formed from a first material such as a hard dielectric, e.g., oxide or nitride, and overcoat 806 may be a second layer formed from a second material such as an organic material. It will be appreciated that either portion of coating 702 is optional. For example, in an embodiment, coating 702 includes filler 804 laterally between the conductors, and coating 702 does not include overcoat 806 such that the top surfaces of the conductors are exposed. Alternatively, coating 702 may include overcoat 806 above the conductors, and coating 702 may not include filler 804 such that a void is present in the dielectric gap laterally between the conductors. Other embodiments of coating 702 may be used. For example, coating 702 may be conformal such that a thin conformal coating, e.g., 2 nanometers thick, is layered over top and lateral surfaces of the conductors and substrate 606. The elongated conductors may have a width or a height greater than the thickness of the conformal coating 702, e.g., 3 microns, and thus, the coating 702 may cover an entire surface of capacitive micro sensor 210, and at least a portion of the dielectric gap between pair of conductors 802 may be unfilled.

Deposition of a material 808 onto any portion of capacitive micro sensor 210 may result in a change in the capacitance of capacitive micro sensor 210. For example, deposition of material 808 onto the interdigitated fingerlike structures shown in FIG. 6 or the coating 702 shown in FIG. 7 may change the capacitance by altering the electric field between pair of conductors 802.

In an embodiment, material 808 deposited onto capacitive micro sensor 210 is a gas. Accordingly, capacitive micro sensor 210 may include several surface area increasing structures. For example, the surface area increasing structures may include fibers, or pores 810, designed to entrap or absorb the gas. For example, coating 702 may include a material, e.g., a porous oxynitride, having a predetermined porosity to absorb gas like a sponge within process chamber 114. When the gas is absorbed by pores 810, the gas may alter the dielectric constant of coating 702, e.g., by increasing the dielectric constant of the bulk material as compared to air-filled pores 810, and the capacitance may change.

Removal of material from capacitive micro sensor 210 may result in a change in the capacitance of capacitive micro sensor 210. For example, removal of material 808 from the interdigitated fingerlike structures or coating 702 may change the capacitance by altering the electric field.

The capacitance change caused by deposition or removal of material 808 may be sensed to determine an amount or a rate of deposition. For example, the change in capacitance can be directly correlated to an amount of material 808 added or removed. Furthermore, given that the capacitance can be monitored in real time, the etch rate, e.g., in angstroms per minute, may be calculated. Preliminary data has indicated that changes in the capacitance of capacitive micro sensors 210 can be measured to detect the presence of particles on capacitive micro sensors 210. Additionally, several capacitive micro sensors 210 may be multiplexed to detect relatively large particles. Similarly, combining capacitive micro sensors 210 may be used to determine particle size.

Material selection of the conductors 602, 604, substrate 606, and coating 702 may be made based on a process that capacitive micro sensor 210 is used to monitor or control. For example, one or more of the structures may be impervious to an etching process that is being monitored. For example, coating 702 may be designed to be removed by the etching process, and substrate 606 may be designed to be impervious to the etching process. Similarly, coating 702 may be removable by the process, and the elongated conductors may not be removable by the process.

The geometry of the structures of capacitive micro sensor 210 may also be designed to correspond to the process being monitored or controlled. For example, when the process includes material deposition, the fingerlike structures may be placed as close to one another as possible to ensure that a detectable capacitance change occurs when material 808 is deposited onto or between the conductors. A thickness of the conductors may also be varied. For example, the interdigitated elongated conductors may be thickened to make the structure more like a parallel plate structure, as opposed to a planar structure.

Figure 9:
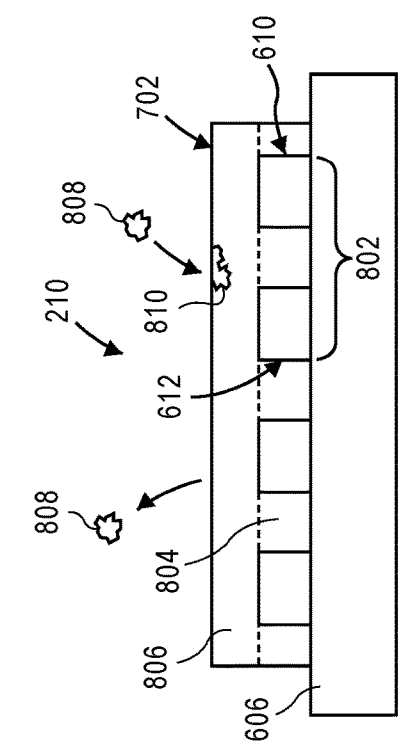
FIG. 9 is a perspective illustration of a capacitive micro sensor of a wafer processing system, in accordance with an embodiment.

Referring to FIG. 9, a perspective illustration of a capacitive micro sensor of a wafer processing system is shown in accordance with an embodiment. Capacitive micro sensor 210 may include a stacked structure. For example, second conductor 604 may be stacked above first conductor 602. The elongated conductors, i.e., first elongated conductors 610 and second elongated conductors 612, may be arranged along a same vertical plane or the elongated conductors may be laterally offset, i.e., interdigitated. In either case, coating 702 may be between first conductor 602 and second conductor 604, and therefore filling the dielectric gap between conductors. In an embodiment, first conductor 602 and second conductor 604 include a grid or mesh structure (not shown) rather than fingerlike structures. The stacked sensor (or any of the sensor structures described) may have conductors of different materials. For example, first conductor 602 may include a metal, and second conductor 604 may include doped polysilicon.

Figure 10:
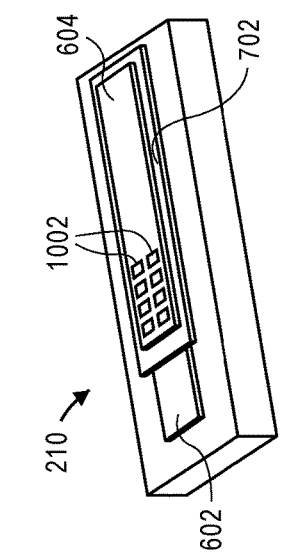
FIG. 10 is a perspective illustration of a capacitive micro sensor of a wafer processing system, in accordance with an embodiment.

Referring to FIG. 10, a perspective illustration of a capacitive micro sensor of a wafer processing system is shown in accordance with an embodiment. Capacitive micro sensor 210 may include a parallel plate structure. For example, first conductor 602 may be a first plate layer, and second conductor 604 may be a second plate layer. Coating 702 may fill the dielectric gap between the plates. In an embodiment, the plate structures are perforated. For example one or more perforations 1002 may extend vertically through first conductor 602 and/or second conductor 604. The parallel plate and/or perforated parallel plate structures may be particularly useful for sensing an isotropic etch profile. In such case, coating 702 between the conductors may include alumina, which has a dielectric constant of 9, to make capacitive micro sensor 210 particularly sensitive to the removal of material 808.

The embodiments of capacitive micro sensors 210 described above are illustrative and not limiting. More particularly, one skilled in the art may conceive of other capacitive micro sensor structures that experience a capacitance change when material is deposited, removed, or modified relative to the sensor structure. Capacitive micro sensors 210 represent one type of micro sensor that may be used in the applications described herein. Other micro sensors may be used, however, in combination with capacitive micro sensors 210 or alone. Several such micro sensor types are described generally below.

Figure 11:
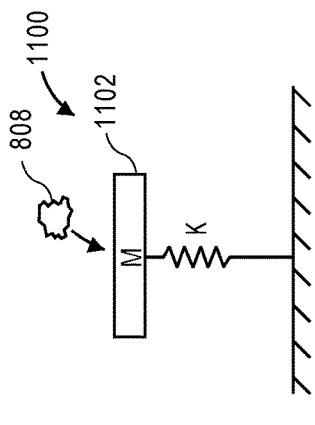
FIG. 11 is a schematic illustration of a micro-resonator type of micro sensor of a wafer processing system, in accordance with an embodiment.

Referring to FIG. 11, a schematic illustrations of a micro-resonator type of micro sensor of a wafer processing system is shown in accordance with an embodiment. In an embodiment, one or more micro sensors of wafer processing tool 102 include a micro-resonator sensor 1100. Micro-resonator sensor 1100 may be a suitable resonant mass sensor, such as a Quartz Crystal Microbalance (QCM), Surface Acoustic Wave (SAW), or Film Bulk Acoustic Resonators (FBAR), which all quantify the cumulative mass 1102 of airborne particles deposited on their surfaces. A description of the complexity and variety of micro-resonator sensors 1100 is not described here in favor of a simplified description for the purpose of brevity and ease of understanding. The micro-resonator sensor(s) 1100 may be distributed at predetermined locations on particle monitoring device 200 or wafer processing tool 102. Each micro-resonator sensor 1100 may have a characteristic frequency, e.g., a resonant frequency, as is known in the art. For example, without going into great detail, micro-resonator sensor 1100 may be represented by a simple mass-spring system. The characteristic frequency of micro-resonator sensor 1100 may be inversely proportional to a mass 1102 of the micro-resonator system. For example, the characteristic frequency may be proportional to $\sqrt{k/M}$ of the micro-resonator sensor 1100, where 'M' corresponds to mass 1102 and 'k' corresponds to a proportionality constant of the micro-resonator sensor 1100. Thus, it will be recognized that the characteristic frequency shifts when micro-resonator sensor 1100 receives or gives off material 808, e.g., during a wafer fabrication process. For example, when material 808, e.g., semiconductor material, is deposited on or removed from a sensor surface of micro-resonator sensor 1100 within process chamber 114 of wafer processing tool 102, mass 1102 of micro-resonator sensor 1100 changes, and accordingly, the characteristic frequency shifts.

In an embodiment, the sensor surface includes material 808. More particularly, the sensor surface may be formed from a same semiconductor material 808 as material 808 deposited on or removed from wafer 402 during a wafer fabrication process. For example, when the wafer fabrication process is a deposition process to deposit silicon onto a silicon wafer 402, the sensor surface may include silicon to ensure that the deposited material 808 interacts with sensor surface in a similar manner to the interaction with wafer 402. Similarly, when the wafer fabrication process is an etching process to remove silicon from the silicon wafer 402, the sensor surface may include silicon to ensure that material 808 is etched from the sensor surface at a similar rate to a removal rate of silicon from the silicon wafer 402. Accordingly, the sensor surface may simulate a surface of the wafer 402 to measure an actual deposition rate or removal rate that is simultaneously occurring to the wafer 402 during the wafer fabrication process.

Figure 12:
FIG. 12 is a schematic illustration of a transistor sensor type of micro sensor of a wafer processing system, in accordance with an embodiment.

Referring to FIG. 12, a schematic illustration of a transistor sensor type of micro sensor of a wafer processing system is shown in accordance with an embodiment. In an embodiment, one or more micro sensors of wafer processing tool 102 include a transistor sensor 1200. Transistor sensor 1200 may include one or more transistor, e.g., a MOSFET 1202. MOSFET 1202 may include a source 1204, a drain 1206, and a gate 1208. Transistor sensor 1200 may also include a collector 1210 to receive or emit material 808 during a wafer fabrication process. Collector 1210 may be physically separated from MOSFET 1202, however, the subcomponents may be electrically connected with each other. For example, collector 1210 may be electrically connected to gate 1208 of MOSFET 1202 through an electrical trace 1212. Thus, MOSFET 1202 may be configured to detect that material 808 has landed on or evaporated from collector 1210 even when collector 1210 is located at a predetermined location spaced apart from MOSFET 1202.

Collector 1210 may be sized and configured to receive material 808. For example, a typical size of material 808 particles may be in a range of 45 nanometers to 1 micron, and thus, collector 1210 may include an outer profile having an outer rim with a diameter of at least 1 micron. A shape of the outer rim when viewed in a downward direction may be circular, rectangular, or any other shape. Furthermore, collector 1210 may be flat, i.e., may have a planar sensor surface, or collector 1210 may have a conical sensor surface. In an embodiment, collector 1210 is not a separate structure from MOSFET 1202, but instead, is incorporated into MOSFET 1202. For example, collector 1210 may be a collection area on gate 1208 of MOSFET 1202.

Similar to micro-resonator sensor 1100 described above, collector 1210 of transistor sensor 1200 may include a sensor surface configured to simulate a surface of wafer 402. For example, transistor sensor 1200 may be located near wafer 402, e.g., on holding surface 412, and sensor surface may be oriented to face a forward direction parallel to a direction faced by a wafer surface. Collector 1210 may include a multi-layer structure, e.g., having a base layer and a top layer of a same or different material.

In an embodiment, a parameter of transistor sensor 1200 corresponds to MOSFET 1202. More particularly, the parameter of transistor sensor 1200 may be a threshold voltage of MOSFET 1202 as measured across gate 1208. The threshold voltage may correspond directly to the presence or absence of material 808 on collector 1210. For example, the threshold voltage may have a first value when a first amount of material 808 is on collector 1210, and the threshold voltage may have a second value (different than the first value) when a second amount of material 808 is on collector 1210. Thus, material 808 collected or emitted from the sensor surface of collector 1210 may be determined based on the threshold voltage of transistor sensor 1200. Processor 508 may be configured to detect a change in the threshold voltage, and thus, when a change in the threshold voltage is detected, wafer processing tool 102 can note the change as a particle detection or an amount of material 808 deposition or removal. The threshold voltage may be logged over time to determine an actual deposition rate or removal rate of material 808 on or from wafer 402.

Figure 13:
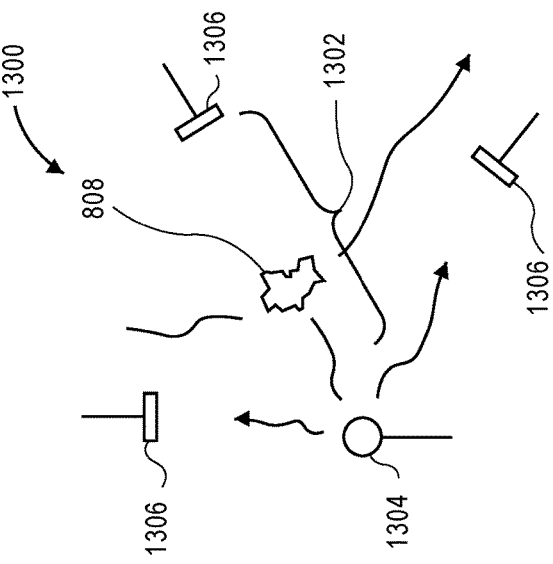
FIG. 13 is a schematic illustration of an optical sensor type of micro sensor of a wafer processing system, in accordance with an embodiment.

Referring to FIG. 13, a schematic illustration of an optical sensor type of micro sensor of a wafer processing system is shown in accordance with an embodiment. In an embodiment, one or more micro sensors of wafer processing tool 102 include an optical sensor 1300. Optical sensor 1300 may be a Micro-Opto-Electro-Mechanical Systems (MOEMS) as is known in the art, and may be formed directly on a substrate using known semiconductor processing operations. A description of the complexity and variety of MOEMS is not described here in favor of a simplified description for the purpose of brevity and ease of understanding. Optical sensor 1300 may include several micro mirrors or lenses distributed across the sensor surface (not shown) of the substrate. Without going into great detail, optical sensor 1300 may include an optical path 1302 emanating from a light source 1304. Optical path 1302 may be between light source 1304 and a light detector 1306. In an embodiment, a parameter of optical sensor 1300 corresponds to whether light is received from light source 1304 at light detector 1306. For example, the parameter may change in response to material 808 disturbing optical path 1302. That is, when particles of material 808 pass through or rest in optical path 1302 and block light between light source 1304 and light detector 1306, the parameter may change. In an embodiment, when particle passes through optical sensor 1300, light from light source 1304 is reflected along a different optical path 1302 toward another light detector 1306. Detection of the reflected light by the other light detector 1306 may result in a change to the parameter of optical sensor 1300. The parameter may be, for example, an output voltage of optical sensor 1300 corresponding to light detection. Processor 508 may be configured to detect a change in the output voltage, and thus, when a change in the output voltage and/or when a disturbance in optical path 1302 is detected, wafer processing tool 102 can note the change as a deposition or removal of material 808 from sensor surface on the substrate, and thus, deposition/removal amounts and/or rates may be measured and monitored in real-time.

It will be appreciated that, since the micro sensor types described above operate on the basis of electrical parameters that are independent of external pressures, particle monitoring device 200 or wafer processing tool 102 having one or more micro sensors such as capacitive micro sensor 210, micro-resonator sensor 1100, transistor sensor 1200, or optical sensor 1300 may work at any pressure regime, including under vacuum conditions. Similarly, the micro sensors may operate regardless of a gaseous consistency of chamber volume 406, including under plasma-less conditions.

Particle monitoring device 200 or wafer processing tool 102 may include any combination of the sensors described above. For example, capacitive micro sensors 210 may be grouped by the thousands on an underlying substrate. More particularly, capacitive micro sensors 210 may be tied in banks so that a base capacitance may be selected by selecting a different number of capacitors from the banks. Such selection may be controlled by processor 508. In an embodiment, processor 508 monitors sensors of different types. For example, a capacitive micro sensor 210 configured to detect material deposition and a capacitive micro sensor 210 configured to detect material etching may be simultaneously monitored, or monitored during different stages of a wafer fabrication process to gather additional data and to form a multipurpose sensor. Similarly, an analog to digital capacitive measurement circuit may be used to monitor capacitive micro sensors 210 at different frequencies to garner additional information. For example, the measurement circuit may probe one or more capacitive micro sensors 210 at a low frequency, a high-frequency, or by sweeping through a wide range of frequencies, to gather additional information.

Wafer processing tool 102 having micro sensors mounted on, e.g., process chamber 114, may be used to monitor or control a wafer fabrication process. While not restrictive, several methods of performing such monitoring and control are described below. For brevity, operations in the methods described below may refer to monitoring of a capacitive micro sensor 210, however, the methods may be adapted to incorporate other micro sensor types, such as the micro sensor types described above.

Referring to FIG. 14, an illustration of a flowchart representing operations in a method of endpointing a wafer fabrication process is shown in accordance with an embodiment. An endpoint of a wafer fabrication process may be detected in some cases by measuring a parameter of the process, e.g., a concentration of a particular element found in plasma 450 within process chamber 114, to determine whether a process operation has achieved a process goal and should be stopped. Such detection may be difficult or impossible using conventional sensors or measurement instruments, however, when chamber volume 406 is plasma-less. The below-described method of determining an endpoint using capacitive micro sensor 210, however, may be used under plasma-less conditions.

At operation 1402, wafer 402 is loaded into process chamber 114 of wafer processing tool 102. Wafer 402 may be formed from a semiconductor material, and may be moved from a first chamber of wafer processing tool 102, e.g., buffer chamber 108, to a second chamber of wafer processing tool 102, e.g., process chamber 114. Accordingly, wafer 402 may be subjected to a wafer fabrication process, e.g., deposition or etching, within chamber volume 406 of process chamber 114.

At operation 1404, the wafer fabrication process may be initiated in process chamber 114. For example, a chamber pressure of the second chamber, e.g., process chamber 114, may be reduced to a vacuum condition. More particularly, the chamber pressure may be lowered below 0.5 atm. As described above, wafer processing tool 102 is capable of detecting material deposition/removal under all pressure regimes, and thus, may be used for real-time monitoring of deposition/removal amount and/or rate under the conditions normally seen by semiconductor wafer 402 in wafer processing tool 102. Accordingly, during the wafer fabrication process, a semiconductor material 808 may be deposited on or removed from wafer 402. Simultaneously, the semiconductor material 808 may be deposited on or removed from capacitive micro sensor 210.

At operation 1406, a change of the capacitance of capacitive micro sensor 210 is detected. More particularly, the change of the capacitance may be detected when material 808 is deposited on or removed from capacitive micro sensor 210 within the second chamber, e.g., process chamber 114. When capacitive micro sensor 210 detects a change in the capacitance, a corresponding signal is provided to electronic circuitry 218.

In an embodiment, the wafer fabrication process is controlled based on the detected change of the capacitance of capacitive micro sensor 210. For example, at operation 1408, the input signal corresponding to the change in the capacitance may be used to determine an endpoint of the wafer fabrication process. For example, the capacitance change may correspond to a deposition of material 808 onto capacitive micro sensor 210 during a deposition process. Similarly, when the wafer fabrication process is an etching process, removal of material 808 from capacitive micro sensor 210 may be detected. An amount of material 808 added or removed may be identical for every process run of wafer processing tool 102. However, if the amount or rate were suddenly more or less, wafer processing tool 102 may determine that a shift in the wafer fabrication process or the process chamber 114 hardware has occurred.

As described above, electronic circuitry 218 of particle monitoring device 200 or wafer processing tool 102 may include a network interface device 506 to transmit and receive communications between wafer processing tool 102 and the host computer. Network interface device 506 may function by a wired or wireless connection 502. In an embodiment, signals may also be transmitted between micro sensors and network interface device 506 wirelessly. More particularly, electronic circuitry 218 may be distributed, such that a wireless transmitter is electrically connected to a micro sensor such as capacitive micro sensor 210, and a wireless receiver is electrically connected to other circuitry of electronic circuitry 218. More particularly, the wireless receiver and the wireless transmitter may both be located within wafer processing tool 102. For example, the wireless transmitter may be mounted on wafer substrate 202 supporting capacitive micro sensor 210, and the wireless receiver may be mounted on chamber wall 404. Data, such as the capacitance of capacitive micro sensor 210, may be communicated between the transmitter and the receiver within wafer processing tool 102. After receiving the data, the wireless receiver may send the received signals to processor 508 or other electronic circuitry 218. Furthermore, the signals may be passed through a wired connection 502 between electronic circuitry 218 and an external computer system 104. The communication between wireless receiver and external computer may be a wired connection 502, e.g., a data cable may be passed through chamber wall 404 of process chamber 114 to communicate data from electronic circuitry 218 to the host computer. Thus, progress of the wafer fabrication process may be measured in real-time. Accordingly, computer system 104 may be configured to detect an endpoint of the process when the desired amount of material 808 is added or removed from capacitive micro sensor 210.

At operation 1410, the wafer fabrication process may be stopped in response to determining the endpoint. For example, when the input signal from capacitive micro sensor 210 indicates that the wafer fabrication process has reached a desired process result, e.g., a predetermined value or change in mass of wafer 402, electronic circuitry 218 or computer system 104 may determine the endpoint of the wafer fabrication process has been reached, and may stop the deposition or etching process based on the input signal.

Referring to FIG. 15, an illustration of a flowchart representing operations in a method of determining a uniformity of a wafer fabrication process is shown in accordance with an embodiment. The wafer fabrication process may be controlled using feedback from capacitive micro sensors 210, e.g., to detect and control process uniformity. By placing several capacitive micro sensors 210 in process chamber 114, an instantaneous uniformity, and a uniformity over time, may be detected. More particularly, changes in a deposition or etching rate at different locations in the process chamber 114 may be sensed to determine whether the deposition or etching process differs between those locations.

Operations 1502 and 1504 may be similar to operations 1402 and 1404 described above with respect to FIG. 14. That is, wafer 402 may be loaded into process chamber 114 of wafer processing tool 102 and the wafer fabrication process may be initiated. At operation 1504, however, the semiconductor material 808 may be deposited on or removed from wafer 402 and several capacitive micro sensors 210 during the wafer fabrication process. That is, deposition or removal of material 808 may be applied to multiple capacitive micro sensors 210 in process chamber 114. For example, a first capacitive micro sensor may be mounted at a first predetermined location on wafer processing tool 102, e.g., within chamber volume 406, and a second capacitive micro sensor may be mounted at a second predetermined location on wafer processing tool 102, e.g., also within chamber volume 406. Material 808 may be deposited on or removed from both of the first and second capacitive micro sensors 210.

At operation 1506, respective changes of the capacitances of each capacitive micro sensor 210 may be detected. For example, a change of a capacitance of the first micro sensor may be detected in response to depositing semiconductor material 808 on or removing semiconductor material 808 from coating 702, elongated conductors, or substrate 606 of the first capacitive micro sensor. Similarly, a change of a capacitance of the second capacitive micro sensor may be detected in response to depositing the semiconductor material 808 on or removing the semiconductor material 808 from coating 702, elongated conductors, or substrate 606 of the second capacitive micro sensor. Accordingly, at a given time, the capacitances of the first capacitive micro sensor and the second capacitive micro sensor may be measured.

At operation 1508, a uniformity of the wafer fabrication process may be determined based on the change of the capacitances of the first and second capacitive micro sensors 210. For example, changes of the capacitances of the several capacitive micro sensors 210 may be measured, and the changes may be compared to detect the uniformity. More particularly, when the changes of the capacitances are the same or similar within a predetermined degree of variation, e.g., within 5% difference, the wafer fabrication process may be determined to be uniform. When the changes of the capacitances vary by a predetermined amount, however, the wafer fabrication process may be determined to be non-uniform. A determination of non-uniformity may trigger an event. For example, a predetermined threshold for a standard deviation between capacitive micro sensors 210 in process chamber 114 may be set, and if the threshold is exceeded, an alarm may be triggered and/or wafer processing tool 102 may be stopped from processing a next wafer. Data gathered from micro sensors may also be saved to a log file locally or on a remote server for future review, e.g., to aid in root cause analysis. Accordingly, wafer processing tool 102 having capacitive micro sensors 210 at several locations may be used to measure and control process stability.

Referring to FIG. 16, an illustration of a flowchart representing operations in a method of determining a root cause of a change of a wafer fabrication process is shown in accordance with an embodiment. Capacitive micro sensors 210 on wafer processing tool 102, e.g., within process chamber 114, may be used to determine a root cause of a particle detection or a change to a deposition or removal rate. For example, capacitive micro sensors 210 may be correlated to other machine sensors to identify a likely cause of a change in deposition or removal rates. In an embodiment, capacitive micro sensor 210 is correlated to a measurement instrument, e.g., an optical spectrometer 416. Alternatively, capacitive micro sensor 210 may be correlated to other machine sensors, such as sensors used to detect temperature, power delivered to process chamber 114, gas concentration, or ion density of process chamber 114.

Operations 1602 through 1606 may be similar to operations 1402 through 1406 described above with respect to FIG. 14. That is, wafer 402 may be loaded into process chamber 114 of wafer processing tool 102 and the wafer fabrication process may be initiated. Furthermore, a change of a capacitance of capacitive micro sensor 210 may be detected.

At operation 1608, a process parameter of the wafer fabrication process may be detected and/or measured by a measurement instrument or device. For example, the measurement instrument may include optical spectrometer 416 described above with respect to FIG. 4. Accordingly, the process parameter may be an OES signature of chamber volume 406 as measured by optical spectrometer 416.

At operation 1610, a root cause of the change of the capacitance of capacitive micro sensor 210 may be determined based on the detected process parameter. For example, the change of the capacitance may occur simultaneously or near in time to a change of the process parameter measured by the measurement instrument. The process parameter may be a concentration of a particular gas, and the change of the process parameter may indicate an increase in the concentration. Accordingly, the concurrent changes may indicate that an increase in the gas concentration is a root cause for the change in the capacitance of the capacitive micro sensor 210, e.g., the root cause for a particle detection or a change in the deposition rate or the removal rate of material 808 on or from capacitive micro sensor 210. Wafer processing tool 102 may then be adjusted or repaired to correct the particle source or to maintain the gas concentration and the deposition/removal rates within a desired range. Accordingly, wafer processing tool 102 having capacitive micro sensors 210 mounted at one or more locations, e.g., on process chamber 114, may be used as a troubleshooting tool.

A change of capacitance of capacitive micro sensors 210 and a detected process parameter may be used to determine other root causes of events within wafer fabrication process, as described below.

Wafer processing tool 102 may include gas lines that carry corrosive materials to and from process chamber 114. Gas lines may be placed under vacuum, and thus, corrosion of gas lines may typically be minimal. Moisture and/or halogens may be introduced into the gas lines, however, when process chamber 114 is opened to perform maintenance without properly purging the gas lines. When gas lines are exposed to moisture and/or halogens, corrosion may occur quite rapidly. Such corrosion may generate particles. Accordingly, in an embodiment capacitive micro sensor 210 is mounted on wafer processing tool 102 at a downstream location from a gas line, or at a location before the gas line reaches process chamber 114. Capacitive micro sensor 210 may be used to detect whether the gas lines are properly purged prior to opening process chamber 114 for maintenance. Capacitive micro sensor 210 may also detect particle excursions in gas lines to detect corrosion. More particularly, gases or corrosion particles may cause a change in capacitance of capacitive micro sensor 210, and the change may be used to determine that the gas or corrosion particle is present in the gas line. When a gas or corrosion particle is detected, appropriate maintenance or repair may be performed on wafer processing tool 102.

After a wafer fabrication process, e.g., an etch or deposition process, halogens or other byproducts may out gas from wafer 402. Techniques exist to abate byproducts, however, it is difficult to quantify how efficient the abatement is and whether wafer 402 is fully out gassed. Wafers 402 that are not fully degassed may lead to queue time issues or contamination by condensation particles. In an embodiment, capacitive micro sensor 210 is mounted on wafer processing tool 102 within load lock 112. Accordingly, capacitive micro sensor 210 measures an amount of halogens or byproducts that are enclosed within a volume of load lock 112. Capacitive micro sensor 210 may thus be used to determine how long and/or when wafer 402 is completely out gassed. Additionally, capacitive micro sensor 210 may be used to detect excursions, or even endpoint a process based on an amount of halogens or byproducts detected in load lock 112. By way of example, capacitive micro sensor 210 may include coating 702 including a material whose electrical properties change depending on what gas it is exposed to. More particularly, coating 702 may absorb gases in load lock 112 having a different dielectric constant than air, and thus, the capacitance of capacitive micro sensor 210 may change when exposed to the gas. When the gas is detected, appropriate repairs or process operations may be performed.

Any moving part in wafer processing tool 102 may be a source of particles. Lift pins move wafer 402 on and off of a chuck or pedestal during a wafer fabrication process. More particularly, lift pins may move wafer 402 from the chuck to a robot, or vice versa. Lift pins may be particle sources both because the pins contact wafer 402, and because the pins may rub against lift pin guides. That is, particles may be generated by lift pin operation. In an embodiment, capacitive micro sensor 210 may be mounted on or in proximity to a lift pin of wafer processing tool 102. Particles generated by lift pins may thus be detected by capacitive micro sensor 210, e.g., by measuring a change in the capacitance of capacitive micro sensor 210. When the particles are detected, appropriate repairs or process operations may be performed.

In the mainframe or factory interface 110, robots fail unexpectedly. When failure occurs, it may lead to long downtime and production interruption. Such interruptions are costly. Therefore, it would be advantageous to be able to predict when a robot will fail long before it actually does. In an embodiment, an accelerometer is mounted on a robot to measure vibration of the robot. An increase in vibration may be indicate, or be an early predictor, of a failing robot. An excursion of vibration data may be identified by comparison to historic values or to a fleet of robots to determine whether vibration data from a particular robot is an outlier. Furthermore, a capacitive micro sensor 210 may be mounted on or in proximity to the robot to detect particles generated by the robot. For example, when a particle is detected by capacitive micro sensor 210, e.g., by a change in the capacitance of capacitive micro sensor 210, it may be inferred that the particle is coming from a particular part, e.g., a joint, slide, lubricant, etc., of the robot. By comparing the data of the accelerometer 514 to the data of capacitive micro sensor 210, the excursions of the sensors may correlate to allow the conclusion to be drawn that the robot is in need of maintenance or repair. As described above, comparisons between data from capacitive micro sensor 210 and other measurement devices of wafer processing tool 102 may allow for correlations and root cause analysis of many different parts. For example, although robots serve as one example, other moving parts such as lift pins, gate lock doors, etc., may be monitored using similar sensor comparisons.

Vacuum source 408 of wafer processing tool 102 may include one or more vacuum pumps. For example, stacks of pumps such as a roughing pump and a turbo pump may be connected to achieve a necessary vacuum level in process chamber 114. Under certain conditions, e.g., when a vacuum pump fails, there may be enough dynamic force to drive particles from one pump to the other pump. More particularly, particles may be driven from a failed roughing pump into a turbo pump and/or chamber volume 406. Such backstreaming can have a negative impact on process chamber 114. Furthermore, it is often not detected, especially when a process manometer result is not logged when the event happens. In an embodiment, capacitive micro sensor 210 is mounted on or in proximity to pressure control valve 414 to detect particles caused by backstreaming. When a particle is detected, e.g., by detecting a change in capacitance of capacitive micro sensor 210, an alarm may be triggered or the event may be logged. Accordingly, the wafer fabrication process may be halted to address the back streaming event and avoid wafer contamination.

In an embodiment, capacitive micro sensors 210 may be used over numerous process runs, and thus, capacitive micro sensors 210 may be self-calibrating to adjust for the deposition or removal of material 808 from coating 702, elongated conductors, or substrate 606. For example, electronic circuitry 218 or computer system 104 may be configured to calibrate capacitive micro sensor 210 after each process run. As material 808 is deposited on or removed from capacitive micro sensor 210 during the wafer fabrication process, the capacitance of capacitive micro sensor 210 may increase or decrease. For example, a mass of capacitive micro sensor 210 may increase after a deposition process, and thus, the capacitance may change from a first value to a second value. Prior to beginning a subsequent deposition process, electronic circuitry 218 or computer system 104 may set the second value as an initial value in the next process run. Accordingly, the change in the capacitance during the next process run may be accurately measured.

Referring to FIG. 17, an illustration of a flowchart representing operations in a method of extending a lifetime of a capacitive micro sensor is shown in accordance with an embodiment. Micro sensors used to monitor or control a wafer fabrication process would ideally last through at least one preventative maintenance cycle. During the wafer fabrication process, byproducts may be deposited on the micro sensors and chamber wall 404. Between runs, a cleaning process may be employed to remove the byproducts to reset the chamber wall 404 and micro sensors to a baseline such that the equipment is essentially the same at the beginning of each process run. It may be useful to understand whether the periodic chamber cleaning is over cleaning. More particularly, it may be useful to detect how much byproduct is removed from chamber wall 404 during the cleaning process, to ensure that the equipment is reset properly. Furthermore, understanding whether the byproducts are effectively removed from the sensor without over cleaning or over-removing sensor material 808, may aid in extending sensor life. That is, by understanding an amount of material 808 added to the micro sensor during the wafer fabrication process, an in situ plasma and chemical cleaning may be used to reset the sensor back to its baseline.

Operations 1702 through 1706 may be similar to operations 1402 through 1406 described above with respect to FIG. 14. That is, wafer 402 may be loaded into process chamber 114 of wafer processing tool 102 and the wafer fabrication process may be initiated. Furthermore, a change of a capacitance of capacitive micro sensor 210 may be detected.

At operation 1708, an amount of material 808 deposited on capacitive micro sensor 210 may be determined based on the change of the capacitance of capacitive micro sensor 210. That is, the amount may be deposited on capacitive micro sensors 210 within chamber volume 406, and the capacitance change may be directly correlated to the deposited amount.

At operation 1710, the amount of material determined to be deposited on capacitive micro sensor 210 may be removed from chamber wall 404 and/or capacitive micro sensor 210. The material may be removed from chamber wall 404 to clean process chamber 114. Capacitive micro sensor 210 may be periodically cleaned or replaced to ensure that a sensitivity and a reliability of capacitive micro sensor 210 is not compromised. For example, when capacitive micro sensor 210 monitors a deposition process, periodic cleaning of capacitive micro sensor 210 may be performed to remove material 808 that is deposited over time. Accordingly, chamber wall 404 and/or capacitive micro sensor 210 may be periodically reset to a baseline cleanliness.

Capacitive micro sensor 210 could be cleaned in situ, without opening process chamber 114, to extend the life of capacitive micro sensor 210. For example, a plasma 450 or radical may be introduced into process chamber 114 to clean material 808 from capacitive micro sensor 210. That is, if material 808 is silicon, then fluorine radicals may be introduced to clean the silicon from sensor surface. In an embodiment, capacitive micro sensor 210 may be heated to speed an etch rate of the sensor coating 702 without over-cleaning chamber wall 404. That is, a removal rate for capacitive micro sensor 210 may be more rapid than for chamber wall 404 while resetting capacitive micro sensor 210 to the baseline, such that the capacitive micro sensor 210 has more byproduct and/or original material removed than chamber wall 404.

Capacitive micro sensors 210 may be replaced on a predetermined periodicity. For example, when capacitive micro sensors 210 are used to monitor an etching process, coating 702 may be consumed over time. Thus, capacitive micro sensors 210 may be replaced when a predetermined amount of material 808, e.g., overcoat 806, has been removed from micro sensor.

Capacitive micro sensors 210 may have uses other than detecting particles or deposition/etch rates during a wafer fabrication process. For example, capacitive micro sensors 210 may be used to accurately measure a DC bias of wafer 402 during the wafer fabrication process and to control the wafer fabrication process based on such measurement.

In a plasma chamber, a negative DC bias, i.e., a negative DC voltage with respect to ground, is applied to wafer 402 to repel lighter electrons and prevent the electrons from hitting wafer 402. The DC bias serves an important function of maintaining quasi-neutrality of plasma 450. The DC bias is also referred to as $V_{dc}$ and plays a role in determining an appropriate chucking voltage to apply to wafer holder 410 to clamp wafer 402. The DC bias, if known, can also be used to estimate the ion energies bombarding the negatively charged wafer 402. Thus, accurate measurement of $V_{dc}$ can be helpful in monitoring and controlling the wafer fabrication process.

Currently, Vdc is estimated based on measurements from voltage and current sensors placed at an output of an RF impedance tuning match. Such measurements, however, are taken remotely from the measured plane and therefore include inherent measurement error. This error is exacerbated at higher RF frequencies, e.g., above 13 MHz, or when additional frequencies are used. Furthermore, the measurements are made using AC signal processing to estimate DC information on the wafer 402, and such processing is prone to error. Accordingly, wafer fabrication process control would benefit from a method of unambiguously measuring $V_{dc}$ without the errors of current techniques.

Figure 18:
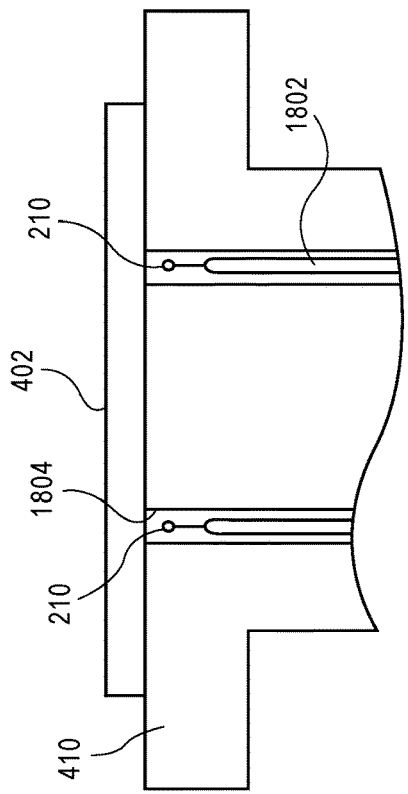
FIG. 18 is a sectional view of a wafer holder incorporating a capacitive micro sensor, in accordance with an embodiment

In an embodiment, the DC bias is measured directly without contacting wafer 402. A noncontact $V_{dc}$ sensor may incorporate capacitive micro sensor 210 positioned near wafer 402 to convert a DC signal to an AC signal for measurement. Referring to FIG. 18, a sectional view of a wafer holder incorporating a capacitive micro sensor is shown in accordance with an embodiment. Direct access to wafer 402 may be obtained by accessing a back side of wafer 402, e.g., through wafer holder 410. More particularly, lift pins 1802 of the current cathode system move along respective lift pin guides having lift pin holes 1804 to lift wafer 402 during certain operations of the wafer fabrication process. Accordingly, capacitive micro sensor 210 may be integrated within lift pin 1802 and/or advanced through lift pin hole 1804 to access the back side of wafer 402. That is, capacitive micro sensor 210 may be mounted on lift pin 1802, or may be separate from lift pin 1802 and able to move through lift pin hole 1804 relative to lift pin 1802. Thus, capacitive micro sensor 210 may be moved to a location adjacent to a DC-biased surface of wafer 400.

Figure 19:
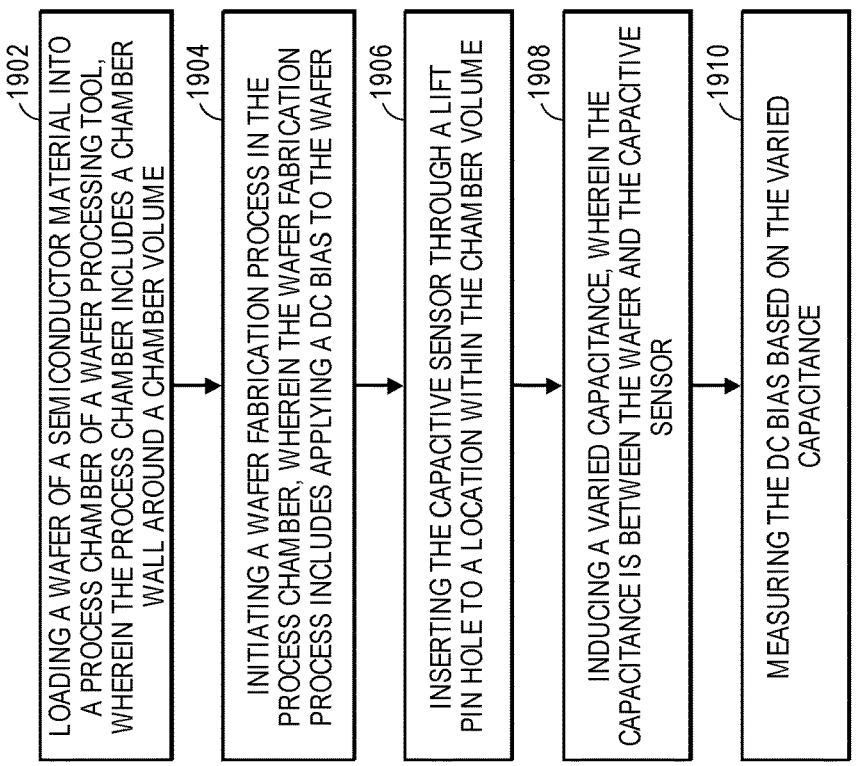
FIG. 19 is an illustration of a flowchart representing operations in a method of measuring DC bias of a wafer during a wafer fabrication process, in accordance with an embodiment.

Referring to FIG. 19, an illustration of a flowchart representing operations in a method of measuring a DC bias of a wafer during a wafer fabrication process is shown in accordance with an embodiment. At operations 1902 and 1904, wafer 402 may be loaded into process chamber 114 of wafer processing tool 102 and the wafer fabrication process may be initiated. The wafer fabrication process may include applying a DC bias to wafer 402.

At operation 1906, capacitive micro sensor 210 may be inserted or advanced through lift pin hole 1804 to a location within chamber volume 406. More particularly, capacitive micro sensor 210 may be positioned near wafer 402 and/or below wafer 402.

At operation 1908, a varied capacitance may be induced. The capacitance may be varied between wafer 402 and capacitive micro sensor 210 either physically or electrically. For example, the capacitance may be varied physically by moving capacitive micro sensor 210 up and down near a surface of wafer 402 while applying a charge to capacitive micro sensor 210. The capacitance may be varied electrically by varying the charge applied to capacitive micro sensor 210. The capacitance of capacitive micro sensor 210 may be proportional to the charge associated with a DC electric field between wafer 402 and capacitive micro sensor 210. Accordingly, the variation in capacitance may result in a variation in the charge, which causes a periodic signal, provided that the induced variation in capacitance is periodic. More particularly, an AC current may be generated in relation to the varied capacitance. In an embodiment, an amplitude of the signal is proportional to a charge stored in wafer 402 that has the negative DC bias.

At operation 1910, the DC bias may be detected or measured based on the varied capacitance. More particularly, the AC current corresponding to the varied capacitance may be measured by electronic circuitry 218. Given that the AC current is generated directly at wafer 402, measurement of the AC current may provide an unambiguous measure of the DC potential of wafer 402, i.e., the DC bias. Accordingly, an accurate measurement of the DC bias may be obtained. The accuracy of the measurement may be enhanced by electronic circuitry 218 using filters to filter out RF fields and to generate currents only associated with the DC bias. More particularly, wafer 402 may experience a displacement current from the main RF signals, and electronic circuitry 218 may filter the displacement current out.

The DC bias measurement may be used as feedback in a control system of wafer processing tool 102. For example, the DC bias measurement may be used to control a chucking voltage of wafer holder 410.

Figure 20:
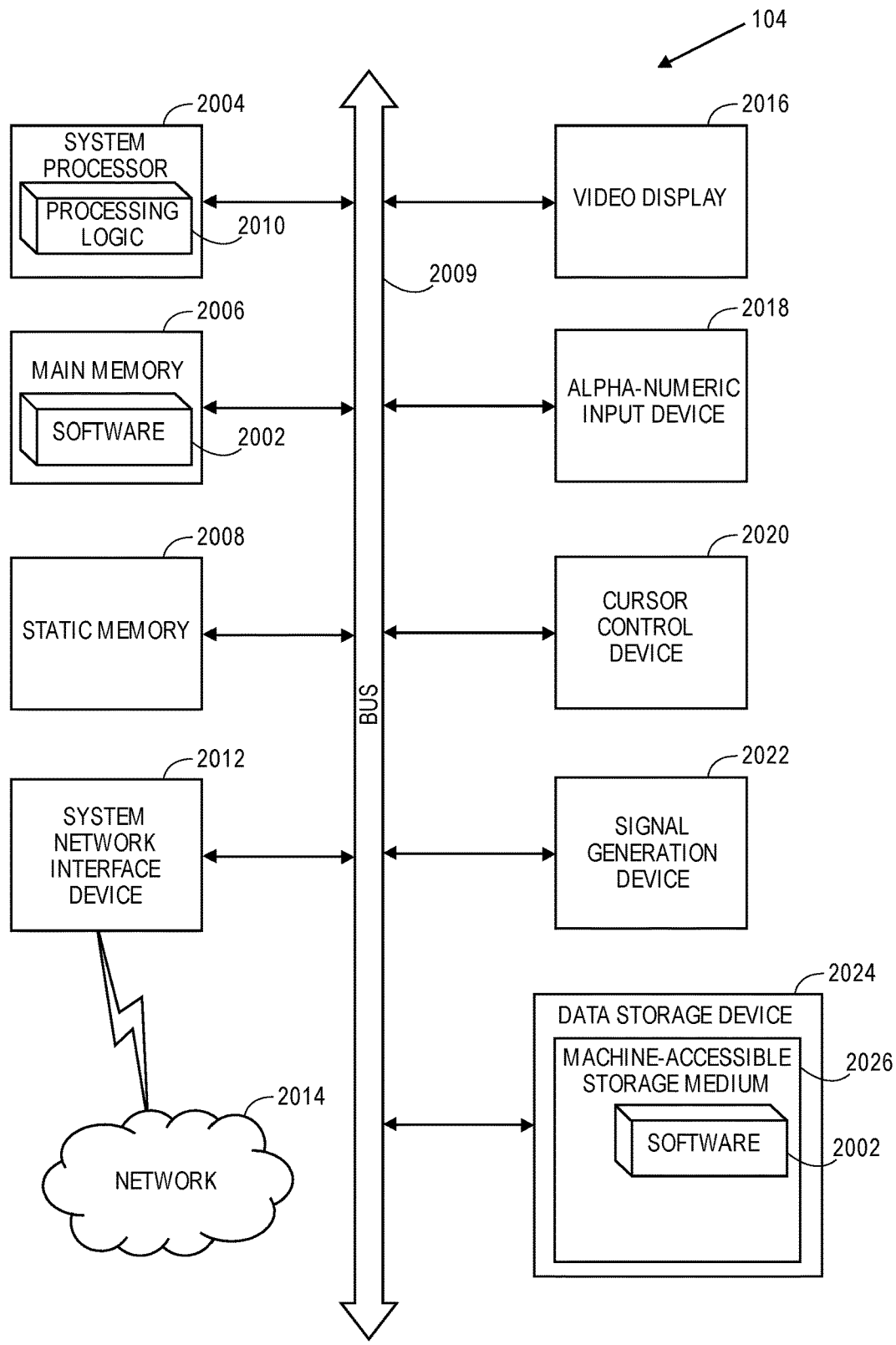
FIG. 20 illustrates a block diagram of an exemplary computer system of a wafer processing system, in accordance with an embodiment.

Referring to FIG. 20, a block diagram of an exemplary computer system of a wafer processing system is shown in accordance with an embodiment. One or more components of the illustrated computer system 104 may be used in electronic circuitry 218 of wafer processing tool 102. Accordingly, electronic circuitry 218 discussed above with respect to FIG. 5 may be a subset of computer system 104. Alternatively, electronic circuitry 218 may be local to particle monitoring device 200 or wafer processing tool 102 and computer system 104 may be a fabrication facility host computer that is interfaced with electronic circuitry 218 and/or a computer of wafer processing tool 102. In an embodiment, computer system 104 is coupled to and controls robots, load locks 112, process chambers 114, and other components of wafer processing tool 102. Computer system 104 may also receive and analyze particle detection or material deposition/removal information provided by capacitive micro sensors 210 as described above.

Computer system 104 may be connected (e.g., networked) to other machines in a Local Area Network (LAN), an intranet, an extranet, or the Internet. Computer system 104 may operate in the capacity of a server or a client machine in a client-server network environment, or as a peer machine in a peer-to-peer (or distributed) network environment. Computer system 104 may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated for computer system 104, the term "machine" shall also be taken to include any collection of machines (e.g., computers) that individually or jointly execute a set (or multiple sets) of instructions to perform any one or more of the methodologies described herein.

Computer system 104 may include a computer program product, or software 2002, having a non-transitory machine-readable medium having stored thereon instructions, which may be used to program computer system 104 (or other electronic devices) to perform a process according to embodiments. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

In an embodiment, computer system 104 includes a system processor 2004, a main memory 2006 (e.g., read-only memory (ROM), flash memory, dynamic random access memory (DRAM) such as synchronous DRAM (SDRAM) or Rambus DRAM (RDRAM), etc.), a static memory 2008 (e.g., flash memory, static random access memory (SRAM), etc.), and a secondary memory (e.g., a data storage device 2024), which communicate with each other via a bus 2009.

System processor 2004 represents one or more general-purpose processing devices such as a microsystem processor, central processing unit, or the like. More particularly, the system processor 2004 may be a complex instruction set computing (CISC) microsystem processor, reduced instruction set computing (RISC) microsystem processor, very long instruction word (VLIW) microsystem processor, a system processor implementing other instruction sets, or system processors implementing a combination of instruction sets. System processor 2004 may also be one or more special-purpose processing devices such as an application specific integrated circuit (ASIC), a field programmable gate array (FPGA), a digital signal system processor (DSP), network system processor, or the like. System processor 2004 is configured to execute the processing logic 2010 for performing the operations described herein.

The computer system 104 may further include a system network interface device 2012 for communicating with other devices or machines, e.g., wafer processing tool 102, over a network 2014. The computer system 104 may also include a video display unit 2016 (e.g., a liquid crystal display (LCD), a light emitting diode display (LED), or a cathode ray tube (CRT)), an alphanumeric input device 2018 (e.g., a keyboard), a cursor control device 2020 (e.g., a mouse), and a signal generation device 2022 (e.g., a speaker).

The secondary memory may include a data storage device 2024 having a machine-accessible storage medium 2026 (or more specifically a computer-readable storage medium) on which is stored one or more sets of instructions (e.g., software 2002) embodying any one or more of the methodologies or functions described herein. The software 2002 may also reside, completely or at least partially, within the main memory 2006 and/or within the system processor 2004 during execution thereof by the computer system 104, the main memory 2006 and the system processor 2004 also constituting machine-readable storage media. The software 2002 may further be transmitted or received over a network 2014 via the system network interface device 2012.

While the machine-accessible storage medium 2026 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies. The term "machine-readable storage medium" shall accordingly be taken to include, but not be limited to, solid-state memories, and optical and magnetic media.

Figure 21:
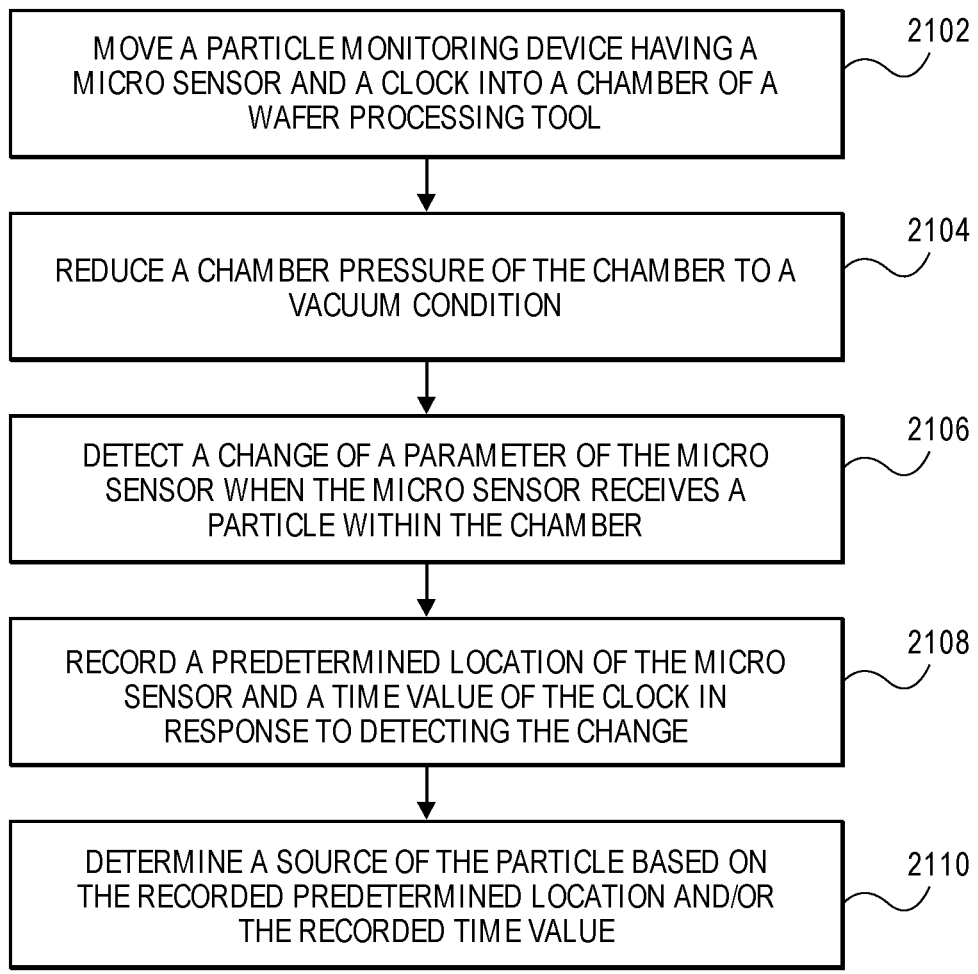
FIG. 21 is an illustration of a flowchart representing operations in a method of determining a source of a particle in a wafer processing tool, in accordance with an embodiment.

The methods described, which use capacitive micro sensors 210 to monitor and/or control wafer fabrication process are illustrative and not exhaustive. More particularly, other methods may incorporate the detection of particles, deposition/etch rates, etc., using capacitive micro sensor 210 to measure and control aspects of a wafer fabrication process performed by wafer processing tool 102. Referring now to FIG. 21, by way of example, an illustration of a flowchart representing operations in a method of determining a source of a particle in a wafer processing tool 102 is illustrated in accordance with an embodiment. At operation 2102, particle monitoring device 200 is moved from a first chamber of wafer processing tool 102, e.g., buffer chamber 108, to a second chamber of wafer processing tool 102, e.g., processing chamber 114. Particle monitoring device 200 may have the structure and components described above, e.g., capacitive micro sensor 210 may be mounted at a predetermined location on support surface 204 and clock 504 may be mounted on substrate 606. Capacitive micro sensor 210 may have a capacitance, and clock 504 may be configured to output a time value.

At operation 2104, a chamber pressure of the second chamber, e.g., processing chamber 114, is reduced to a vacuum condition. More particularly, the chamber pressure may be lowered below 0.5 atm. As described above, particle monitoring device 200 is capable of detecting particles under all pressure regimes, and thus, may be used for real-time particle monitoring under the conditions normally seen by semiconductor wafer 402 in wafer processing tool 102.

At operation 2106, a change of the capacitance of capacitive micro sensor 210 is detected. More particularly, the change of the capacitance may be detected when capacitive micro sensor 210 receives a particle within the second chamber, e.g., processing chamber 114. When capacitive micro sensor 210 (or electronic circuitry 218 connected to capacitive micro sensor 210) detects a change in the capacitance, a corresponding signal is provided.

At operation 2108, the corresponding signal is used by processor 508 to record information about the particle event in response to detecting the change of the capacitance. For example, processor 508 may record the predetermined location of micro sensor on support surface 204. Accordingly, the precise location where particle interacts with particle monitoring device 200 may be recorded. Processor 508 may record the time value output by clock 504. Accordingly, the precise time when particle interacts with particle monitoring device 200 may be recorded.

At operation 2110, the recorded information may be used to determine a source of particle. For example, the recorded predetermined location of capacitive micro sensor 210 that received the particle and/or the recorded time value corresponding to the particle event may be used to determine the component and/or the process operation performed by wafer processing tool 102 that led to the particle contamination.

In an embodiment, the recorded time value acts as a timestamp that can be synchronized with a log file of wafer processing tool 102. For example, wafer processing tool 102 may maintain a log file indicating a time at which every process operation begins and/or ends. Thus, by comparing the time value output by clock 504 (when the particle is detected by capacitive micro sensor 210) to the log file, a process operation concurrent with the particle event may be determined. By way of example, if the time value output indicates that the particle event occurred 5 minutes into the wafer fabrication process, and the system log file indicates that a slit valve door of load lock 112 was opened at the 5 minute mark, it may be reasonably concluded that the slit valve door, and/or the action of opening load lock 112, is a source contributing to particle being ejected toward particle monitoring device 200.

In a similar manner to the timestamp information, the information about the location of particle contact may be used to determine the particle source. For example, when several process operations occur simultaneously, e.g., lift pins 1802 rise when a slit valve door closes, a relative distance between the particle location and the active components may be used to infer which component is the source of the particle. That is, if the recorded location is nearer to the lift pins 1802 than to the slit valve door, it may be inferred that the lift pins 1802 are the source of the particle.

The information about particle contamination may be continuously logged during the wafer fabrication process, and thus, the information may be made available for analysis in real-time or in near real-time. That is, particle monitoring device 200 may be connected wirelessly to other machines in a network 2014 using a wireless network interface device 506 to monitor and analyze particle contamination data using a computer system 104 remotely situated from particle monitoring device 200 in real-time. Alternatively, particle monitoring device 200 may be connected to the other machines via a data transfer cable as soon as particle monitoring device 200 completes the wafer fabrication process of wafer processing tool 102 to analyze stored information in near real-time. Similarly, when particle monitoring device 200 comes out of wafer processing tool 102 after the wafer fabrication process, contacts connected to electronic circuitry 218 and/or capacitive micro sensors 210 may be manually probed to receive and log data for process control. Thus, a source of particle contamination may be quickly identified during or after the wafer fabrication processes is complete, and appropriate repairs may be made. Particle monitoring device 200 may be used as a process qualification operation prior to running batches of semiconductor wafers 402 through the wafer fabrication process of wafer processing tool 102. Alternatively, particle monitoring device 200 may be used as a process troubleshooting tool to facilitate timely repairs of wafer processing tool 102 when particle contamination is identified within a batch of semiconductor wafers 402. Accordingly, particle monitoring device 200 provides a fast, inexpensive, and easy way to identify and eliminate a source of particle contamination in wafer processing tool 102.

In the foregoing specification, specific exemplary embodiments have been described. It will be evident that various modifications may be made thereto without departing from the scope of the following claims. The specification and drawings are, accordingly, to be regarded in an illustrative sense rather than a restrictive sense.

What is claimed is:

1. A particle monitoring device, comprising:
   a wafer substrate including wafer electronics and a support surface;
   a capacitive micro sensor mounted on the support surface at a location, wherein a capacitance of the capacitive micro sensor changes when a material is deposited on or removed from the capacitive micro sensor; and
   a barrier layer between the capacitive micro sensor and the wafer substrate, wherein the capacitive micro sensor is electrically connected to the wafer electronics through the barrier layer, and wherein the capacitive micro sensor is strippable by a plasma and the barrier layer is not strippable by the plasma.

2. The particle monitoring device of claim 1, wherein the capacitive micro sensor includes a pair of conductors having a first conductor and a second conductor mounted on a substrate, wherein the first conductor includes a plurality of first elongated conductors, and wherein the second conductor includes a plurality of second elongated conductors interdigitated with the plurality of first elongated conductors.

3. The particle monitoring device of claim 2, wherein the capacitive micro sensor includes a coating over one or more of the first conductor or the second conductor, wherein the coating includes the material, and wherein the capacitance of the capacitive micro sensor changes when the material is removed from the coating.

4. The particle monitoring device of claim 2, wherein the capacitive micro sensor includes a coating over one or more of the first conductor or the second conductor, wherein the coating includes a plurality of pores, and wherein the capacitance of the capacitive micro sensor changes when the material is deposited in the pores.

5. The particle monitoring device of claim 1, wherein the wafer electronics includes a processor operably coupled to the capacitive micro sensor to record the location when the capacitance changes.

6. The particle monitoring device of claim 5, wherein the wafer substrate includes a top layer and a bottom layer, and further comprising a power source between the top layer and the bottom layer, wherein the power source is electrically coupled to the processor to power the processor.

7. The particle monitoring device of claim 6 further comprising a barrier seal between the top layer and the bottom layer around the power source.

8. A wafer processing tool, comprising:
a process chamber having a chamber wall around a chamber volume; and
a capacitive micro sensor mounted on the wafer processing tool at a location, wherein a capacitance of the capacitive micro sensor changes in response to a wafer fabrication process performed by the wafer processing tool, wherein the capacitive micro sensor is mounted on one or more of a load lock, a gas line, a robot, or a pressure control valve of the wafer processing tool.

9. The wafer processing tool of claim 8, wherein the capacitive micro sensor includes a pair of conductors having a first conductor and a second conductor mounted on a substrate, wherein the first conductor includes a plurality of first elongated conductors, and wherein the second conductor includes a plurality of second elongated conductors interdigitated with the plurality of first elongated conductors.

10. The wafer processing tool of claim 9, wherein the capacitive micro sensor includes a coating over one or more of the first conductor or the second conductor, wherein the coating includes a material, and wherein the capacitance of the capacitive micro sensor changes when the material is removed from the coating during the wafer fabrication process.

11. The wafer processing tool of claim 9, wherein the capacitive micro sensor includes a coating over one or more of the first conductor or the second conductor, wherein the coating includes a plurality of surface area increasing structures, and wherein the capacitance of the capacitive micro sensor changes when a material is deposited in the surface area increasing structures during the wafer fabrication process.

12. A method, comprising:
loading a wafer of a semiconductor material into a process chamber of a wafer processing tool, wherein the process chamber includes a chamber wall around a chamber volume, wherein the wafer includes a DC bias;
initiating a wafer fabrication process in the process chamber, wherein a material is deposited on or removed from the wafer during the wafer fabrication process;
detecting, in response to the wafer fabrication process, a change of a capacitance of a capacitive micro sensor mounted on the wafer processing tool at a location;
controlling, based on the detected change, the wafer fabrication process; and
inserting the capacitive micro sensor through a lift pin hole to the location within the chamber volume;
inducing a varied capacitance, wherein the capacitance is between the wafer and the capacitive micro sensor; and
measuring the DC bias based on the varied capacitance.

13. The method of claim 12, wherein the capacitance changes when the material is deposited on or removed from the capacitive micro sensor during the wafer fabrication process, and wherein the location is in proximity to one or more of the chamber wall, a lift pin, a load lock, a gas line, a robot, or a pressure control valve of the wafer processing tool.

14. The method of claim 13 further comprising:
determining an endpoint of the wafer fabrication process based on the change of the capacitance; and
stopping the wafer fabrication process in response to determining the endpoint.

15. The method of claim 13, wherein the wafer processing tool includes a second capacitive micro sensor mounted on the wafer processing tool at a second location, and further comprising:
detecting, in response to the wafer fabrication process, a change of a second capacitance of the second capacitive micro sensor; and
determining a uniformity of the wafer fabrication process based on the change of the capacitance of the capacitive micro sensor and the change of the second capacitance of the second capacitive micro sensor.

16. The method of claim 13 further comprising:
detecting, by a measurement device, a process parameter of the wafer fabrication process; and
determining a root cause of the change of the capacitance of the capacitive micro sensor based on the detected process parameter.

17. The method of claim 13 further comprising:
determining, based on the change of the capacitance of the capacitance sensor, an amount of the material deposited on the capacitive micro sensor within the chamber volume during the wafer fabrication process; and
removing, based on the determined amount, the amount of the material from the chamber wall to clean the process chamber.

18. A method, comprising:
loading a wafer of a semiconductor material into a process chamber of a wafer processing tool, wherein the process chamber includes a chamber wall around a chamber volume;
initiating a wafer fabrication process in the process chamber, wherein a material is deposited on or removed from the wafer during the wafer fabrication process;
detecting, in response to the wafer fabrication process, a change of a capacitance of a capacitive micro sensor mounted on the wafer processing tool at a location; and controlling, based on the detected change, the wafer fabrication process, wherein the capacitance changes when the material is deposited on or removed from the capacitive micro sensor during the wafer fabrication process, and wherein the location is in proximity to one or more of the chamber wall, a lift pin, a load lock, a gas line, a robot, or a pressure control valve of the wafer processing tool, wherein the wafer processing tool includes a second capacitive micro sensor mounted on the wafer processing tool at a second location, and the method further comprising:

detecting, in response to the wafer fabrication process, a change of a second capacitance of the second capacitive micro sensor; and determining a uniformity of the wafer fabrication process based on the change of the capacitance of the capacitive micro sensor and the change of the second capacitance of the second capacitive micro sensor.

* * * * *